US009491946B2

(12) United States Patent
Santra et al.

(10) Patent No.: US 9,491,946 B2
(45) Date of Patent: Nov. 15, 2016

(54) AG LOADED SILICA NANOPARTICLE/NANOGEL FORMULATION, METHODS OF MAKING, AND METHODS OF USE

(71) Applicant: University of Central Florida Research Foundation, Inc., Orlando, FL (US)

(72) Inventors: Swadeshmukul Santra, Orlando, FL (US); Roseline Menezes, Newark, NJ (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 0 days.

(21) Appl. No.: 13/664,460

(22) Filed: Oct. 31, 2012

(65) Prior Publication Data

US 2013/0108678 A1    May 2, 2013

Related U.S. Application Data

(60) Provisional application No. 61/554,267, filed on Nov. 1, 2011.

(51) Int. Cl.
| *A01N 59/16* | (2006.01) |
| *A01N 59/20* | (2006.01) |
| *B82Y 30/00* | (2011.01) |
| *A01N 25/04* | (2006.01) |

(52) U.S. Cl.
CPC ............... *A01N 59/16* (2013.01); *A01N 59/20* (2013.01); *B82Y 30/00* (2013.01)

(58) Field of Classification Search
USPC .......................... 977/773, 777, 778, 810, 915
See application file for complete search history.

(56) References Cited

U.S. PATENT DOCUMENTS

| 2,913,419 | A | 4/1956 | Alexander |
| 3,983,214 | A | 9/1976 | Misato et al. |
| 3,992,146 | A | 11/1976 | Fazzalari |
| 5,462,738 | A | 10/1995 | LeFiles et al. |
| 5,939,357 | A | 8/1999 | Jones et al. |
| 6,471,976 | B1 | 10/2002 | Taylor et al. |
| 6,548,264 | B1 | 4/2003 | Tan et al. |
| 6,924,116 | B2 | 8/2005 | Tan et al. |
| 7,147,921 | B2 | 12/2006 | Camp et al. |
| 7,163,709 | B2 | 1/2007 | Cook et al. |
| 7,226,610 | B2 | 6/2007 | Winniczuk |
| 7,332,351 | B2 | 2/2008 | Tan et al. |
| 8,221,791 | B1 | 7/2012 | Santra |
| 8,246,933 | B2 * | 8/2012 | Jiang et al. ..................... 424/46 |
| 8,361,437 | B2 | 1/2013 | Sharma et al. |
| 2001/0051174 | A1 | 12/2001 | Staats |
| 2004/0067247 | A1 | 4/2004 | DeSloovere et al. |

(Continued)

OTHER PUBLICATIONS

Kim et al. "Silver-nanoparticle dispersion forms the consolidation of Ag-attached silica colloid", J. Mater. Res., vol. 19, No. 5, (May 2004).*

(Continued)

*Primary Examiner* — Ernst V Arnold
*Assistant Examiner* — Kyung Sook Chang
(74) *Attorney, Agent, or Firm* — Bond, Schoeneck & King, PLLC; William Greener; Alek Szecsy

(57) ABSTRACT

Embodiments of the present disclosure, in one aspect, relate to compositions including a silver/silica nanocomposite, methods of making a silver/silica nanocomposite, methods of using a silver/silica nanocomposite, and the like.

11 Claims, 20 Drawing Sheets

(56) References Cited

U.S. PATENT DOCUMENTS

| | | |
|---|---|---|
| 2004/0091417 A1 | 5/2004 | Yadav |
| 2005/0084438 A1 | 4/2005 | Do et al. |
| 2006/0018966 A1 | 1/2006 | Lin et al. |
| 2007/0009672 A1* | 1/2007 | Jeong et al. ............ 427/523 |
| 2007/0098806 A1 | 5/2007 | Ismail et al. |
| 2010/0015236 A1 | 1/2010 | Magdassi et al. |

OTHER PUBLICATIONS

Xu et al. "Fabrication of antibacterial monodispersed Ag—SiO2 core-shell nanoparticles with high concentration", Material Letters, published by Elsevier B.V., pp. 31-33 (2009).*

"Coating of Nanosize Silver Particles with Silica", Journal of Colloid and Interface Science 221, pp. 133-136 (2000).*

MSDS of isopropyl alcohol [retrieved from on-line website: http://www.cvear.com/wp-content/uploads/2012/06/Isopropyl-Alcohol-70-MSDS.pdf, last visit Sep. 7, 2015].*

Zhang, X. A New Solution Route to Hydrogen-terminated Silicon Nanoparticles; Synthesis, Functionalization and Water Stability, Jan. 2007, Nanotechnology, vol. 18, pp. 1-6.

Yeshchenko, Oleg, Influence of Annealing Conditions on Structure and Optical Properties of Copper Nanoparticles Embedded in Silica Matrix, 2006, Physics Department, National Taras Shevchenko Kyiv University, Ukraine, pp. 1-25.

Kikteva, T.A., Probing the Sol-Gel Conversion in the Tetraethoxysilane/Alcohol/Water System with the Aid of Diffusion-Controlled Flourescence Quenching, 1997, Journal of Colloid and Interface Science, vol. 193, pp. 163-166.

The International Search Report and Written Opinion mailed Jan. 2, 2012.

Kim, Y.H., et al., "Preparation and characterization of the Antibacterial Cu Nanoparticle Formed on the Surface of SiO2 Nanoparticles," J. Phys. Chem B 2006, vol. 110, pp. 24923-24928.

Barik, T.K., et al., "Nanosilica-From MEdicine to Pest Control," Parasitol, Res 2008, vol. 103, pp. 253-258.

Sebastien Dugravot et al. Dimethyl Disulfide Exerts Insecticidal Neurotoxicity Through Mitochondrial Dysfunction and Activiation of KATP Channels Journal of Neurophysciology; 2003, 8 pages.

Zhang, K., Synthesis and Characterization of Silica-Copper Oxide Composite Derived from Microemulsion Processing, 1999, Langmuir, vol. 15, pp. 3056-3061.

S. Santra, et al., in "Fluorescence Lifetime Measurements to Determine the Core-Shell Nanostructure of FITC-doped Silica Nanoparticles: An Optical Approach to Evaluate Nanoparticle Photostability" Journal of Luminescence, 2006, 117(1) pp. 75-82.

Oberdorster, G., et al., in Nanotoxicology: An Emerging Discipline Evolving from Studies of Ultrafine Particles, Environmental Health Perspectives, 2005, 113(7): pp. 823-839.

Navarro, E., et al., in "Environmental behavior and ecotoxicity of engineered nanoparticles to algae, plants, and fungi," Ecotoxicology, 2008, 17(5): pp. 372-386.

Torgeson D.C .. ed. "Fungicides-An Advanced Treatise" Agricultural and Industrial Applications and Enviromental Interaction. vol. 1. 1967. Academic Press: New York. NY, Ch. 6, p. 153-193 [chapter Title: Formulation: Author: E. Somers.

H.W. Richardson, "Handbook of Copper Compounds and Applications" Copper Fungicides/batericides H.W. Richardson Editor, 1997, Marcel Dekker, Inc.: New York, NY, pp. 93-122.

Maniprasad, et al.; Antimicrobial Properties of Copper and Silver Loaded Silica Nanomaterials; Manuscript ID No. 1198620; to be submitted to the 36th International Conference on Advanced Ceramics and Composites (ICACC); Apr. 4, 2012.

Naik, et al., "Biomimetic synthesis and patterning of silver nanoparticles." Nature Materials 1, 169-172 (2002).

Mock, et al., "Shape effects in plasmon resonance of individual colloidal silver nanoparticles." Journal of Chemical Physics 116, 6755-6759 (2002).

Manipradad, et al.; Novel Copper (Cu) Loaded Core-Shell Silica Nanoparticles with Improved Cu Bioavailability: Synthesis, Characterization and Study of Antibacterial Properties; Journal of Biomedical Nanotechnology; vol. 8, 1-9, 2012.

Cho, et al., "The Study of Antimicrobial Activity and Preservative Effects of Nanosilver Ingredient", Electrochimica Acta 51,956-960 (2005).

Feng, et al. "A Mechanistic Study of the Antibacterial Effect of Silver Ions on *Escherichia coli* and *Staphylococcus aureusI*", Journal of Biomedical Materials Research 52, 662-668 (2000).

Jasiorski, et al., "Textile with silver Silica Spheres: its Antimicrobial Activity against *Escherichia coli* and *Staphylococcus aureus*", Journal of Sol-Gel Science and Technology 51, 330-334 (2009).

Hu, et al., "A Simple and Effective Route for the Synthesis of Crystalline Silver Nanrods and Nanowires", Advanced Functional Materials 14, 183-189 (2004).

Solomon, et al. (2007). "Synthesis and study of silver nanoparticles." Journal of Chemical Education. 84, 322-325.

Pal, et al. (2007). "Does the antibacterial activity of silver nanoparticles depend on the shape of the nanoparticle? A study of the gram-negative bacterium *Escherichia coli*." Applied Environmental Microbiology 73, 1712-1720.

Jung, et al. (2008). Antibacterial activity and mechanism of action of the silver ion in *Staphylococcus aureus* and *Escherichia coli*. Applied Environmental Microbiology 74, 2171-2178.

Frisken, B. J. (2001). "Revisiting the method of cumulants for the analysis of dynamic light-scattering data." Applied Optics 40, 4087-4091.

Schillinger, et al. (1989). "Antibacterial Activity of Lactobacillus-Sake Isolated from Meat." Applied and Environmental Microbiology 55, 1901-1906.

Rastogi, et al., "Ag colloids and Ag clusters over EDAPTMS-coated silica nanoparticles:synthesis, characterization, and antibacterial activity against *Escherichia coli*." Nanomedicine-Nanotechnology Biology and Medicine 7, 305-314 (2011).

Collins, T.J., "ImageJ for Microscopy Biotechniques." 43, 25-30(2007).

* cited by examiner

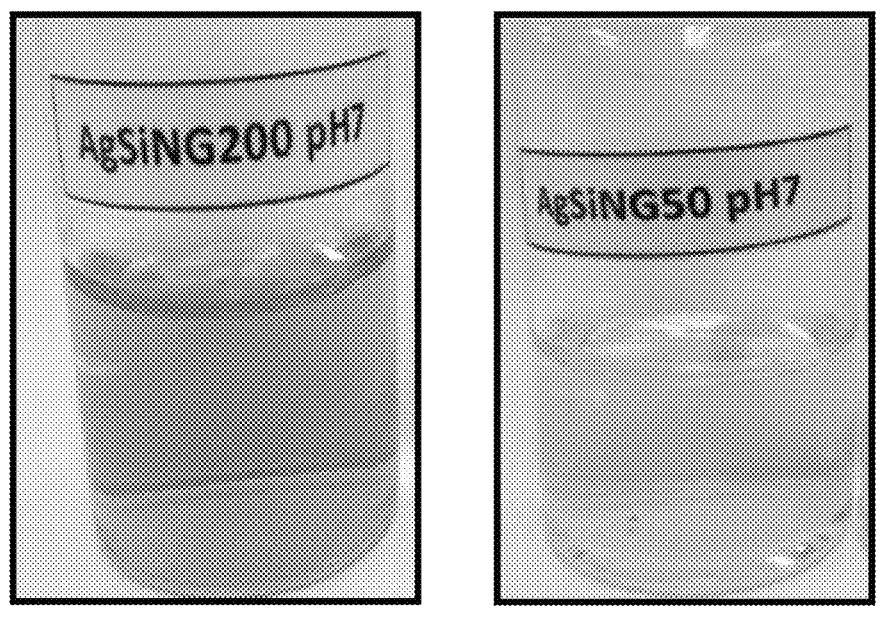
(a) (b)
FIG. 1.1

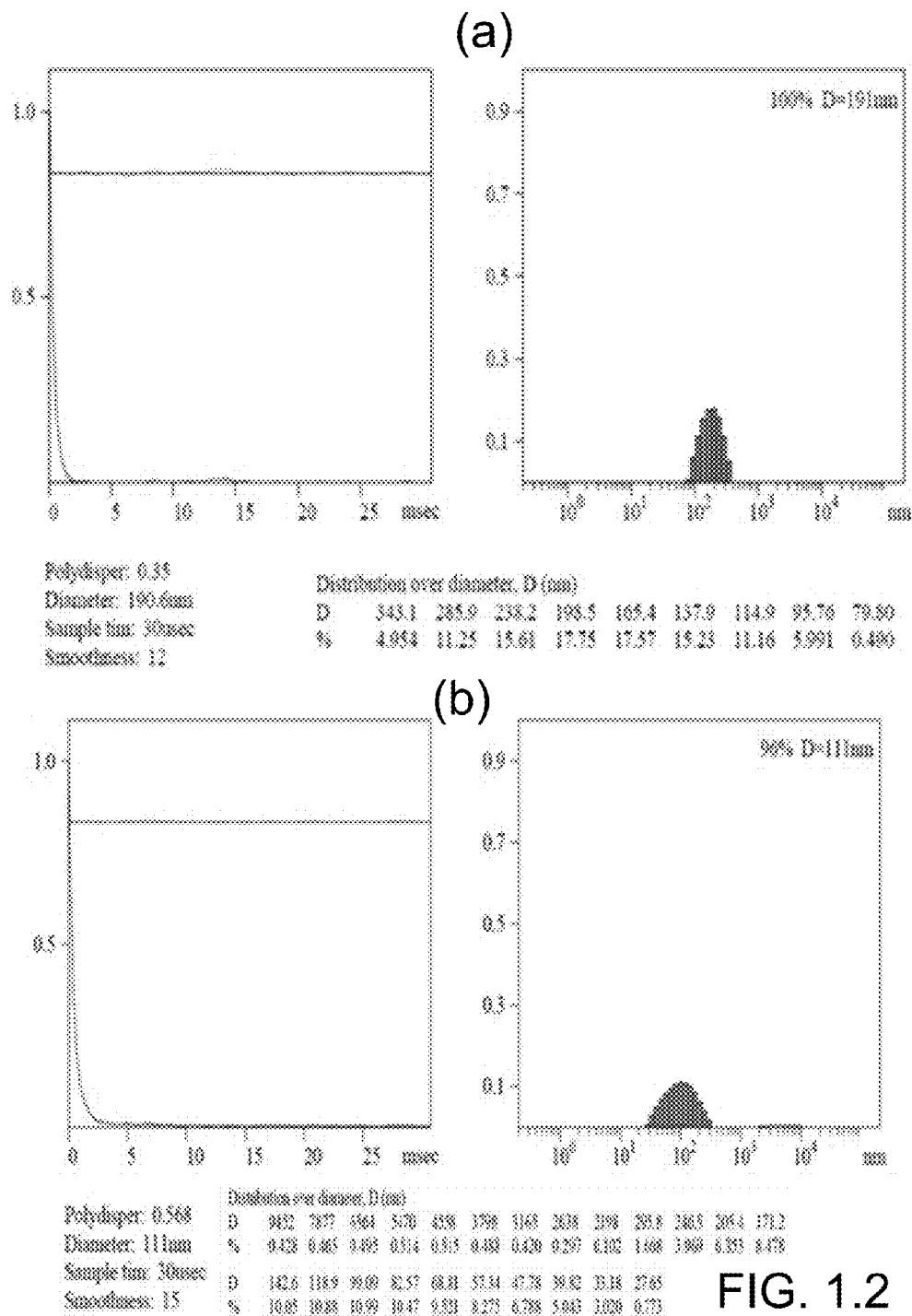
FIG. 1.2

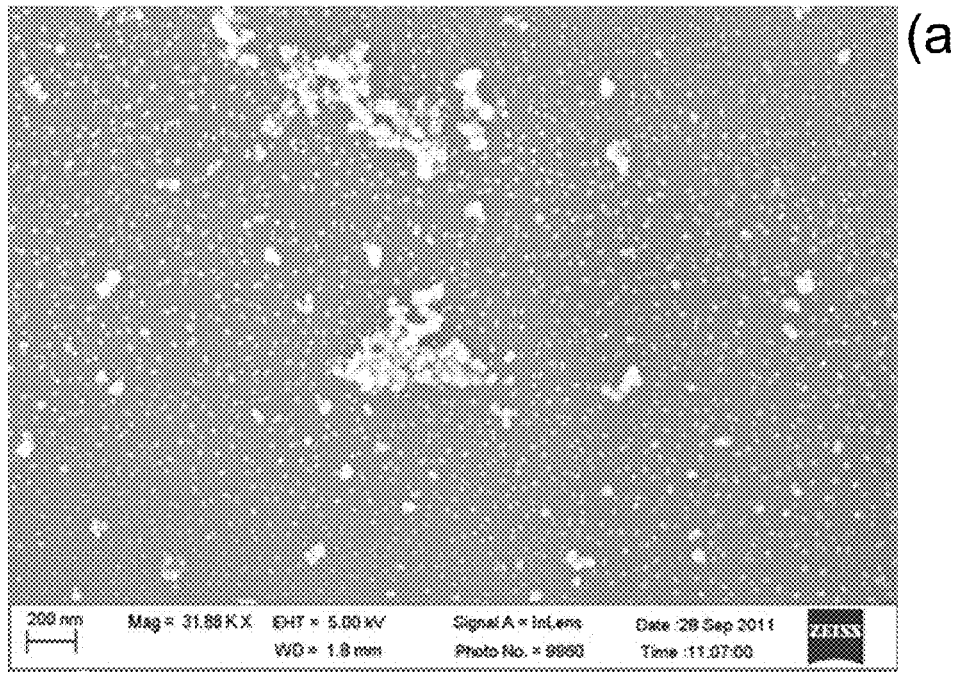
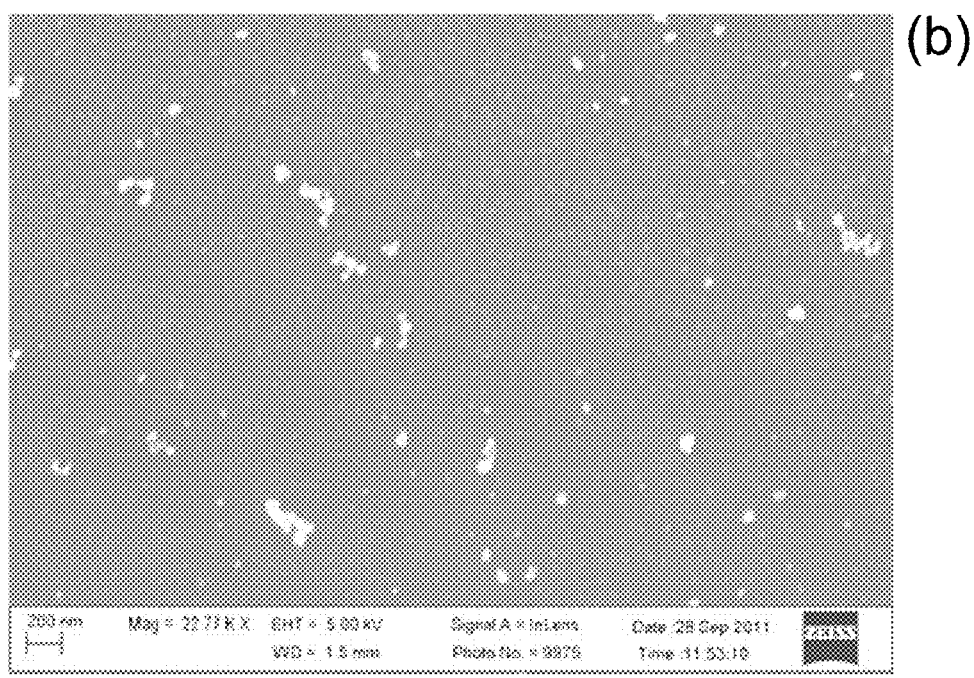
FIG. 1.3

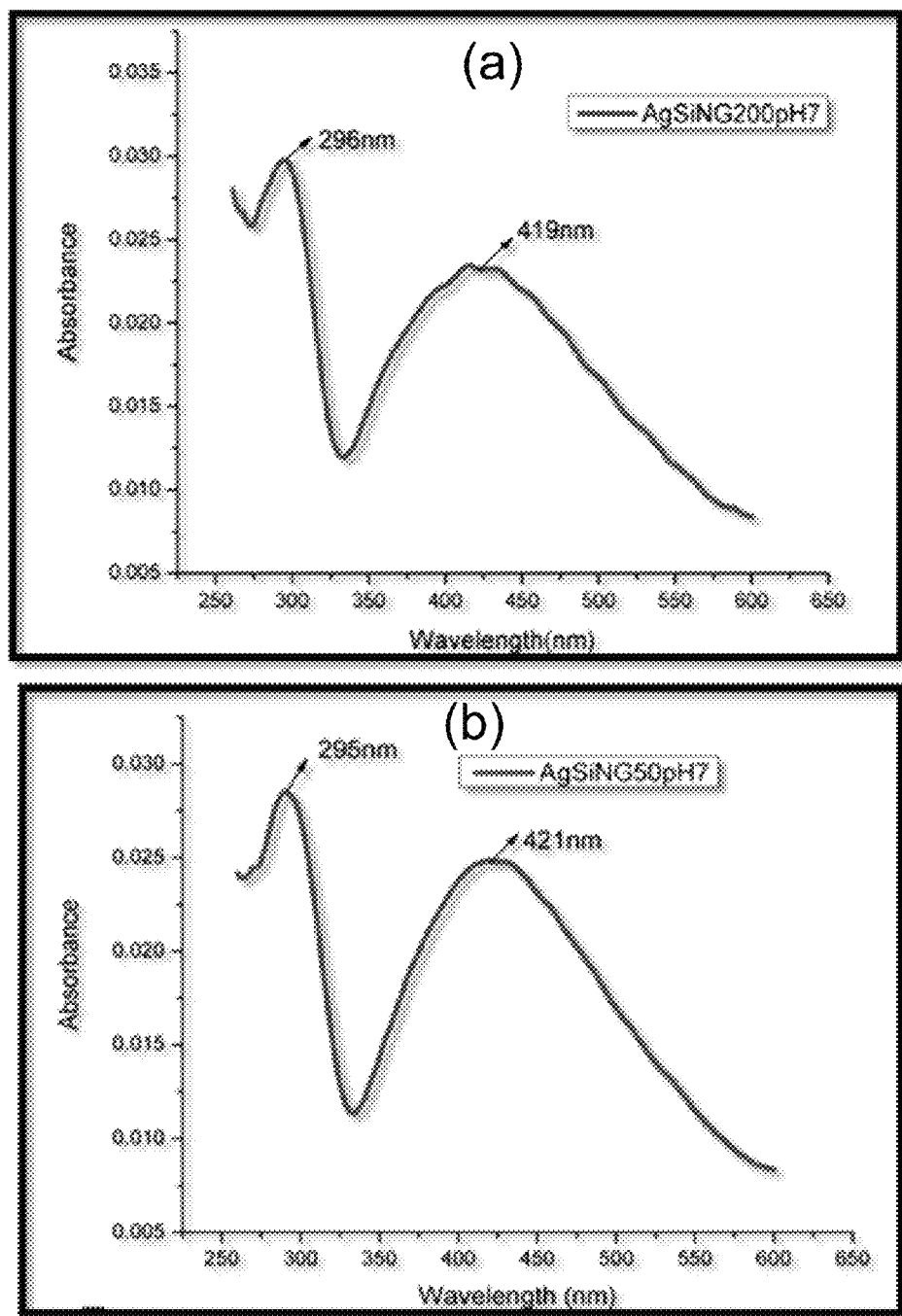
FIG. 1.4

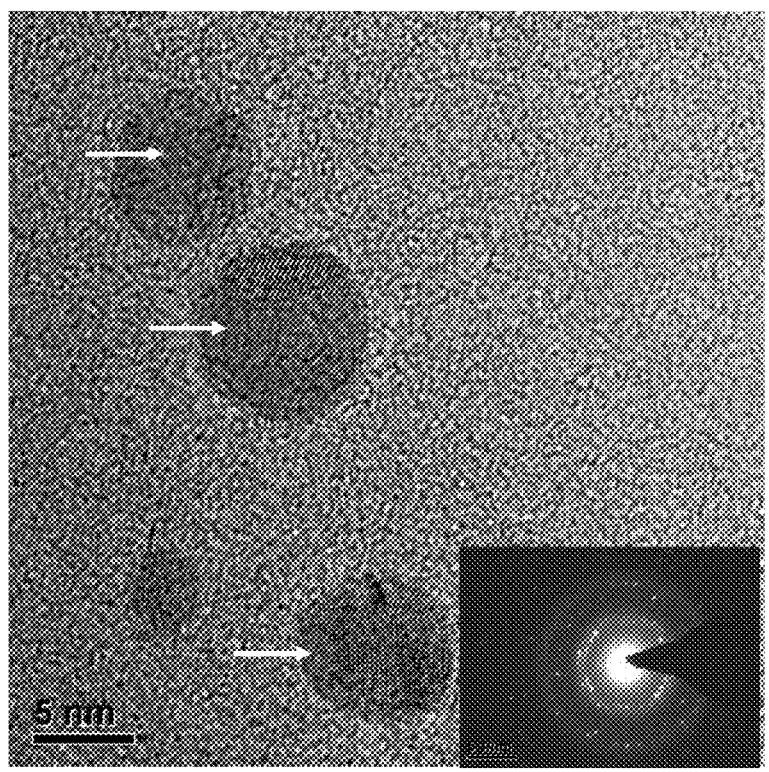
(a)
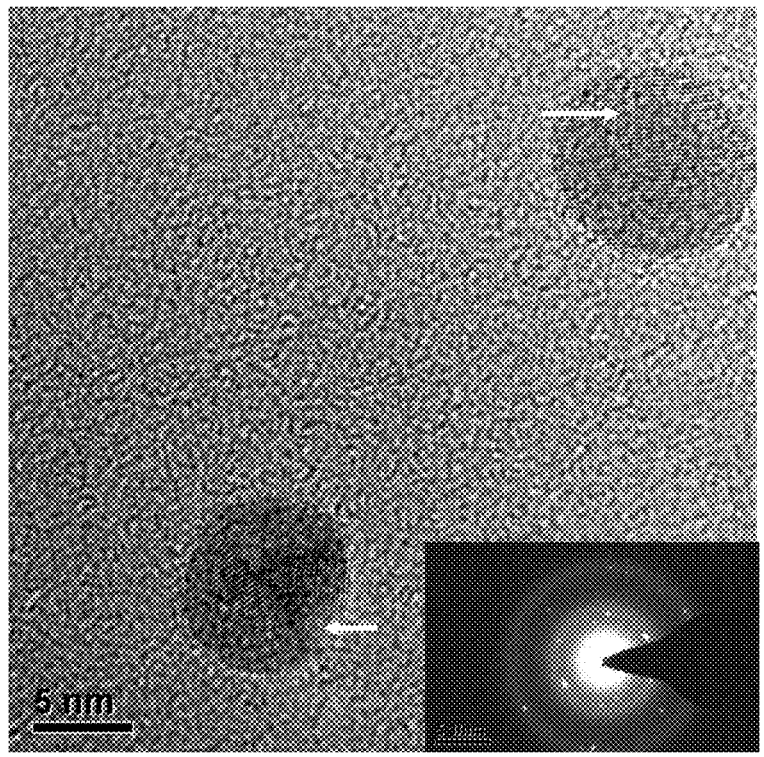
(b)
FIG. 1.5

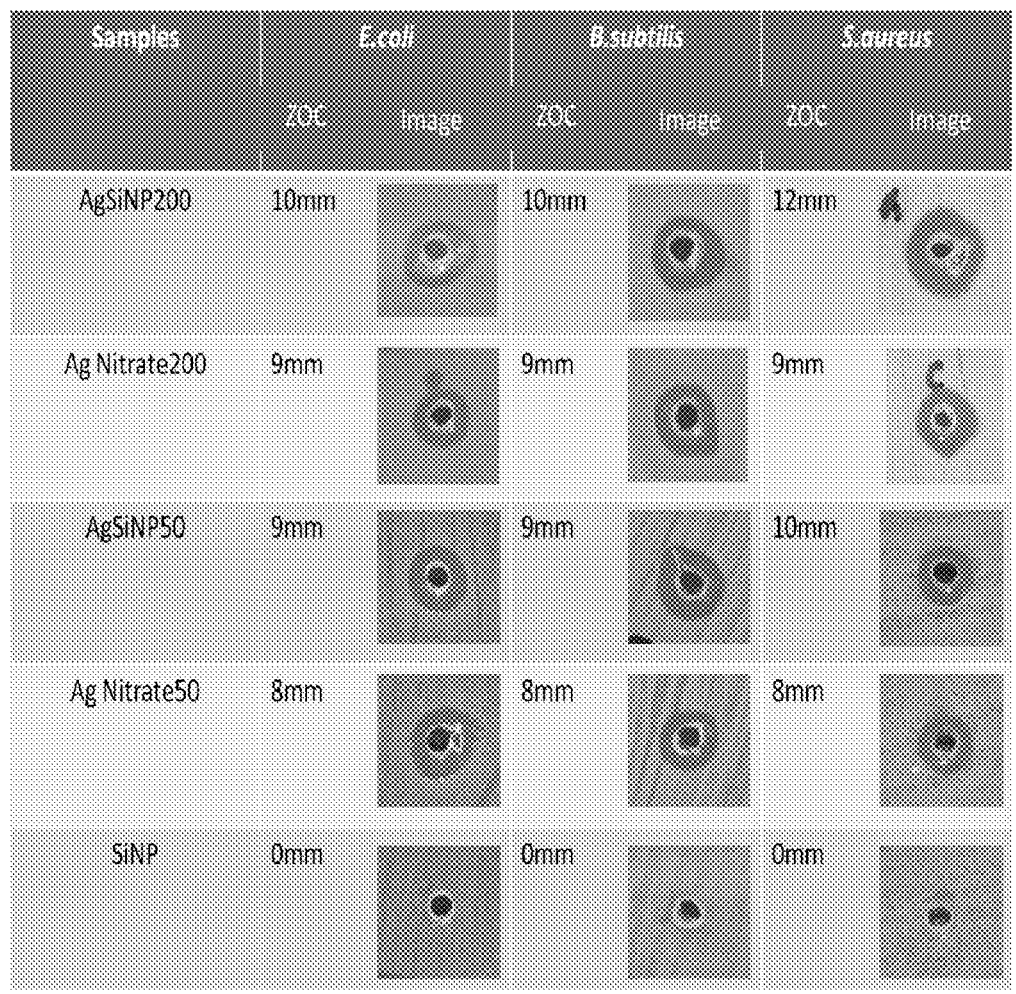
FIG. 1.6

Figure 1.7
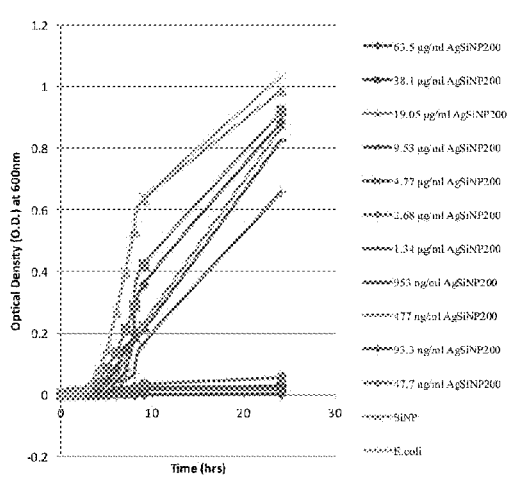
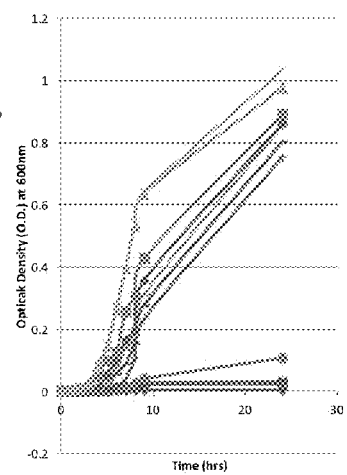
(a)
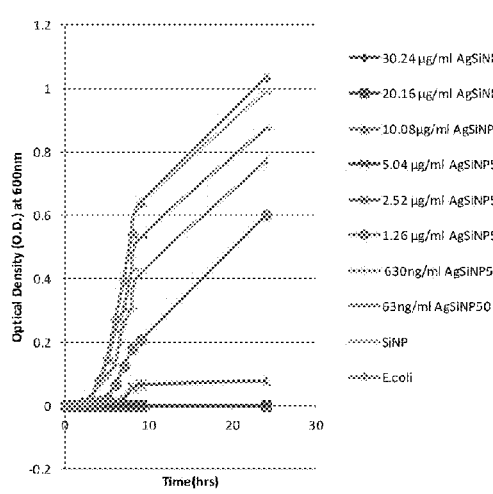
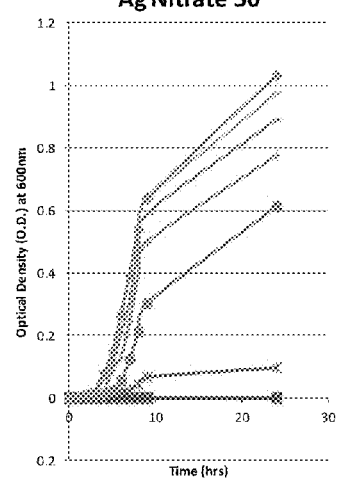
(b)

Figure 1.8
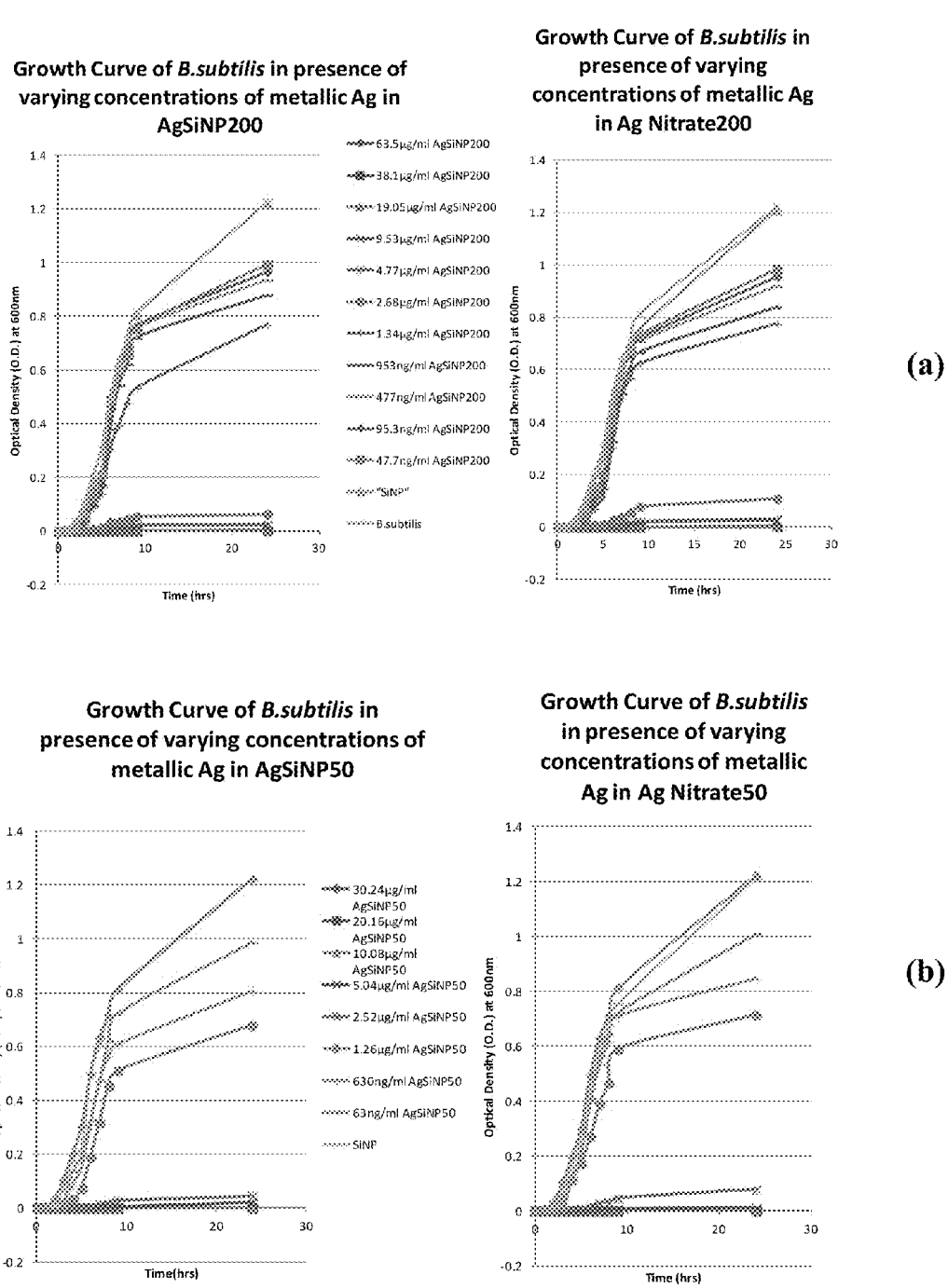

Figure 1.9
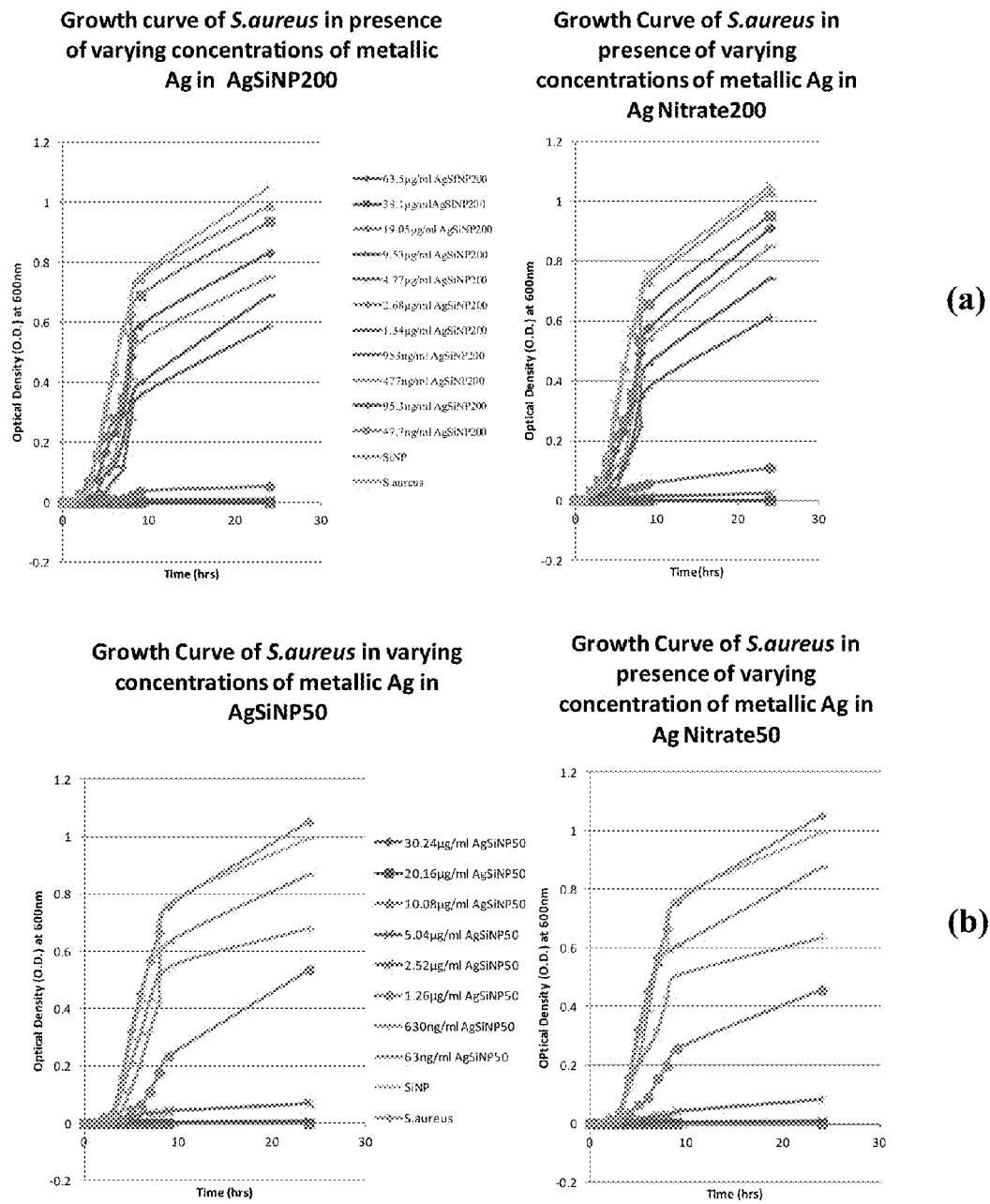

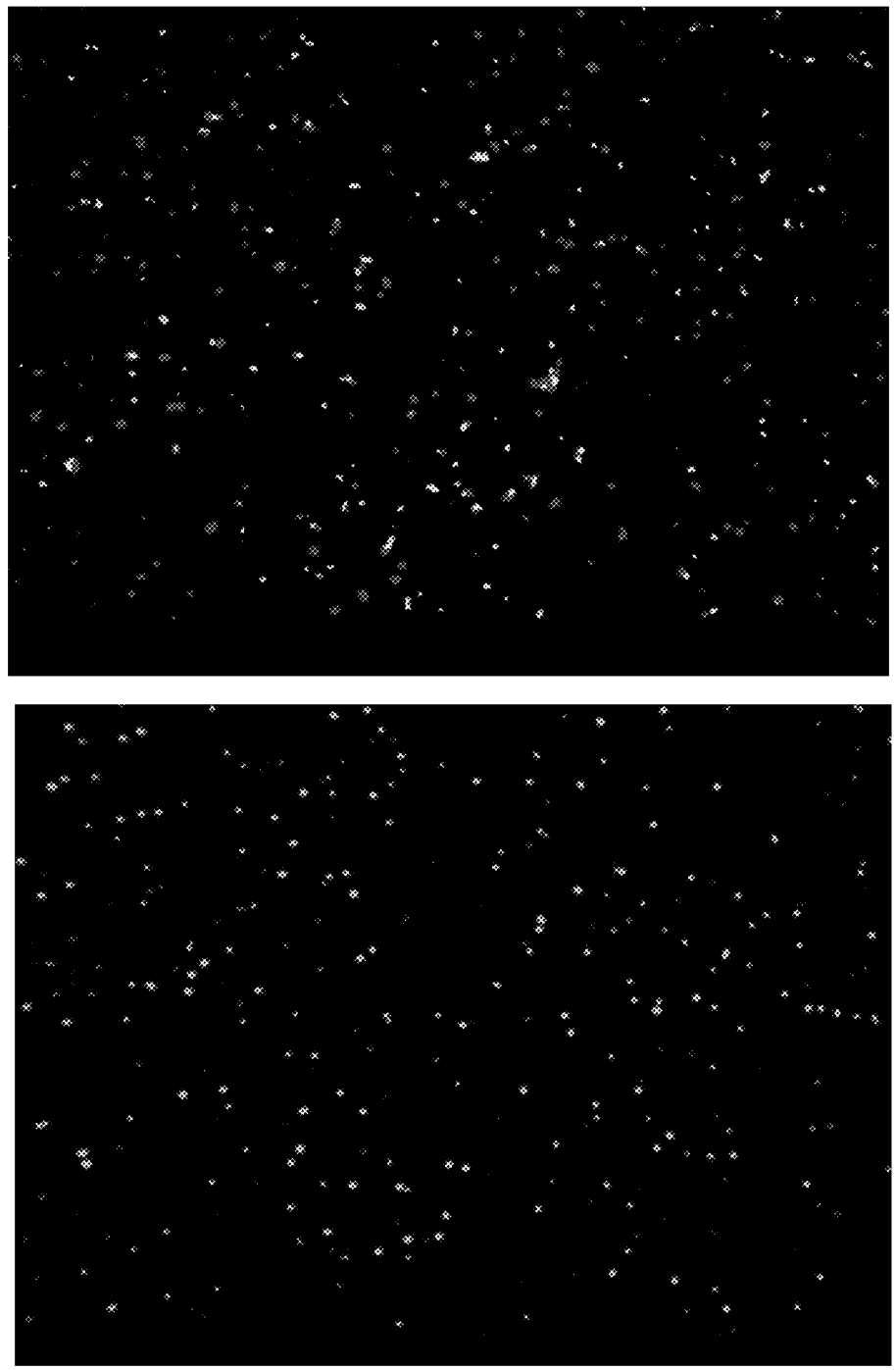
FIG. 1.10

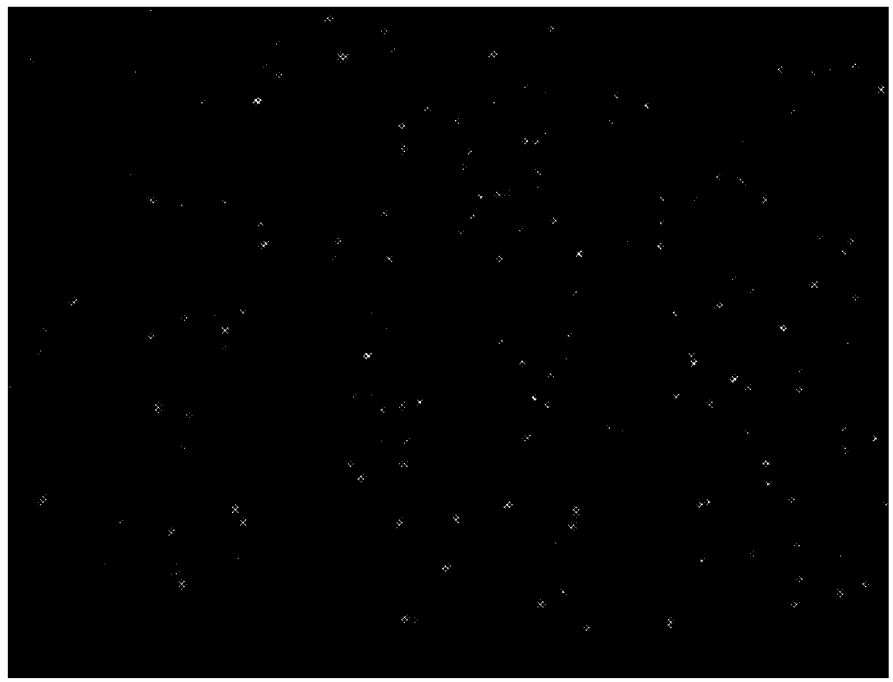
(a)
(b)
FIG. 1.11

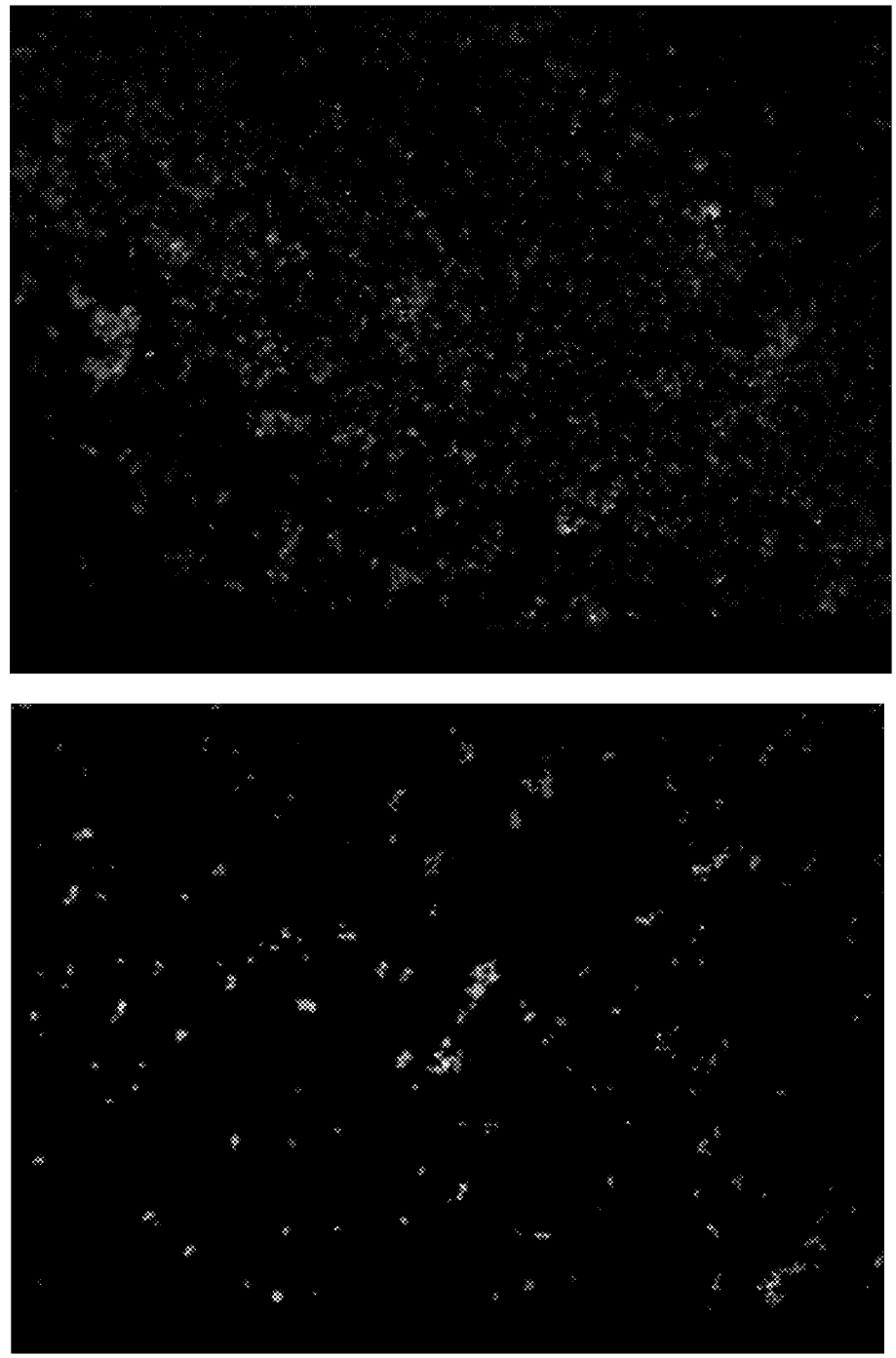
FIG. 1.12

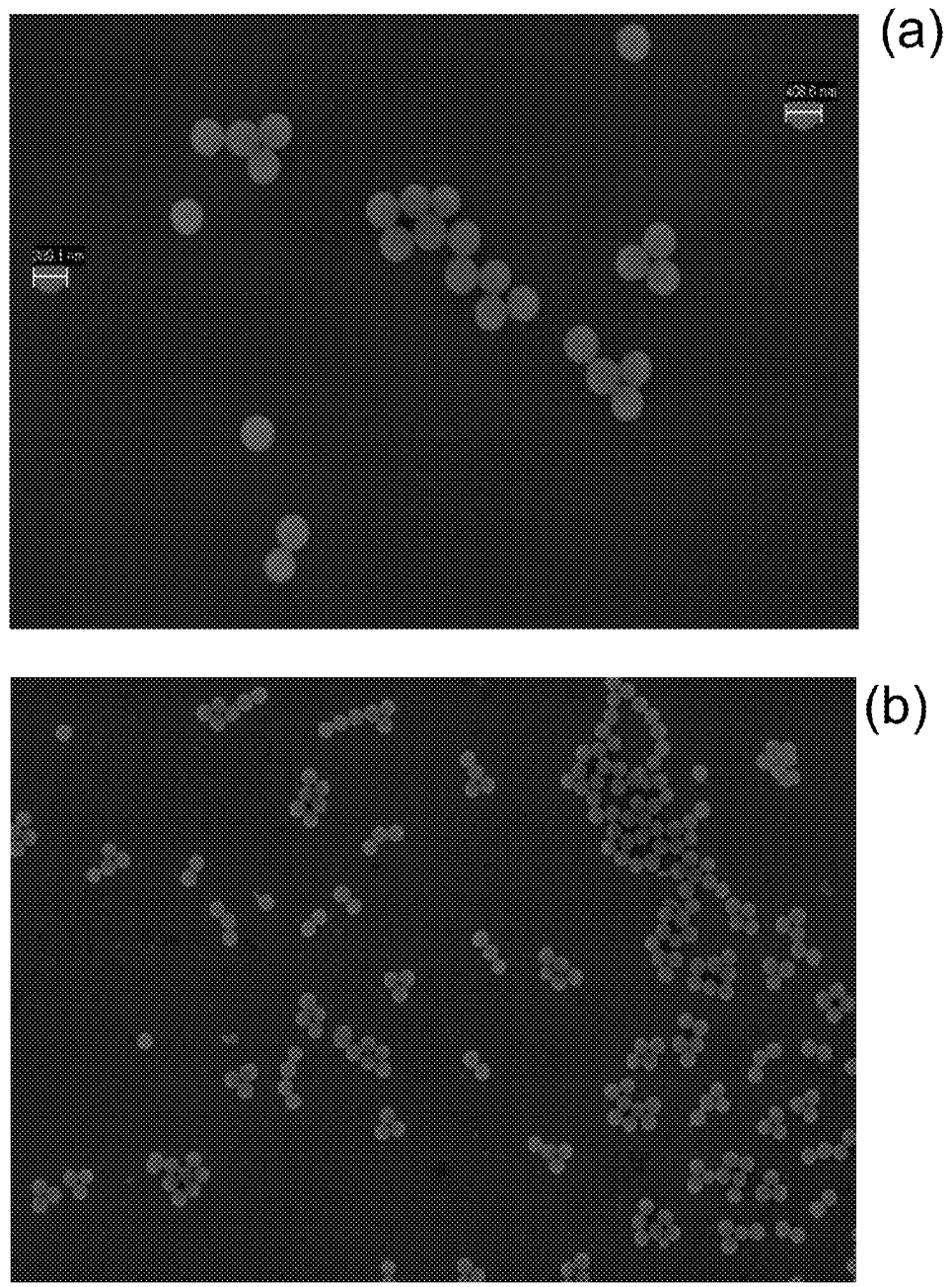
FIG. 2.1

(a)
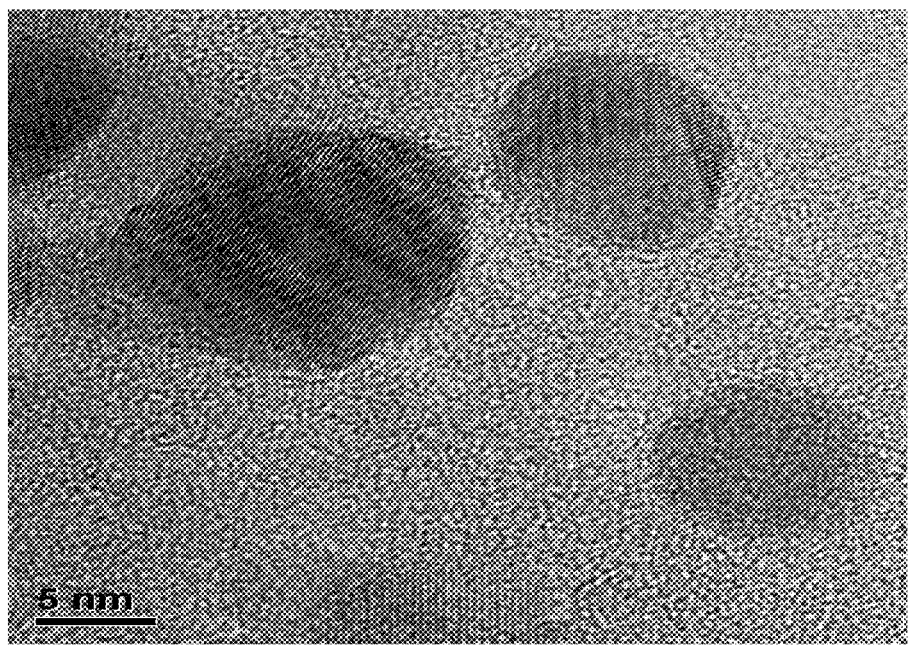
(b)
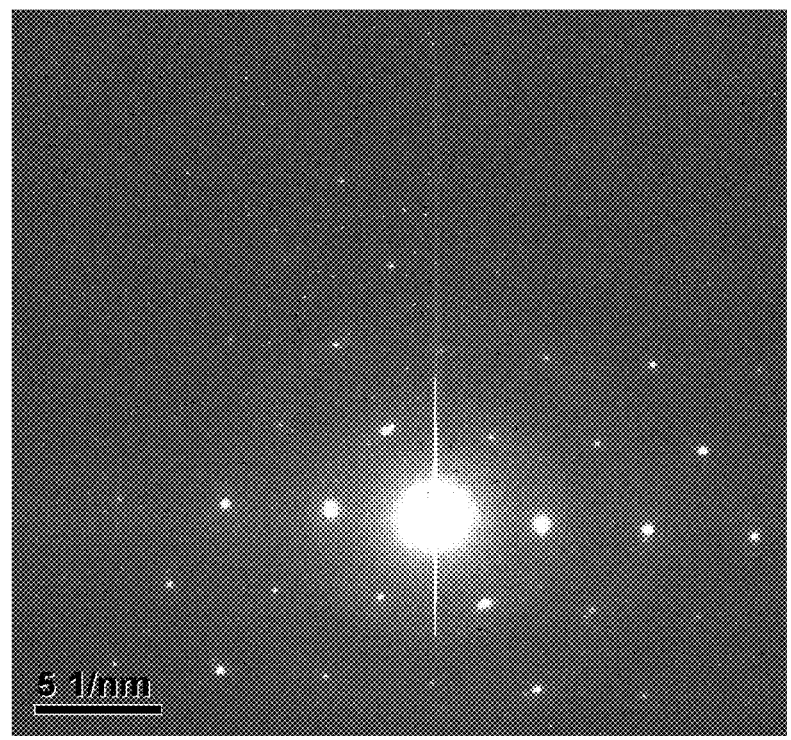
FIG. 2.2

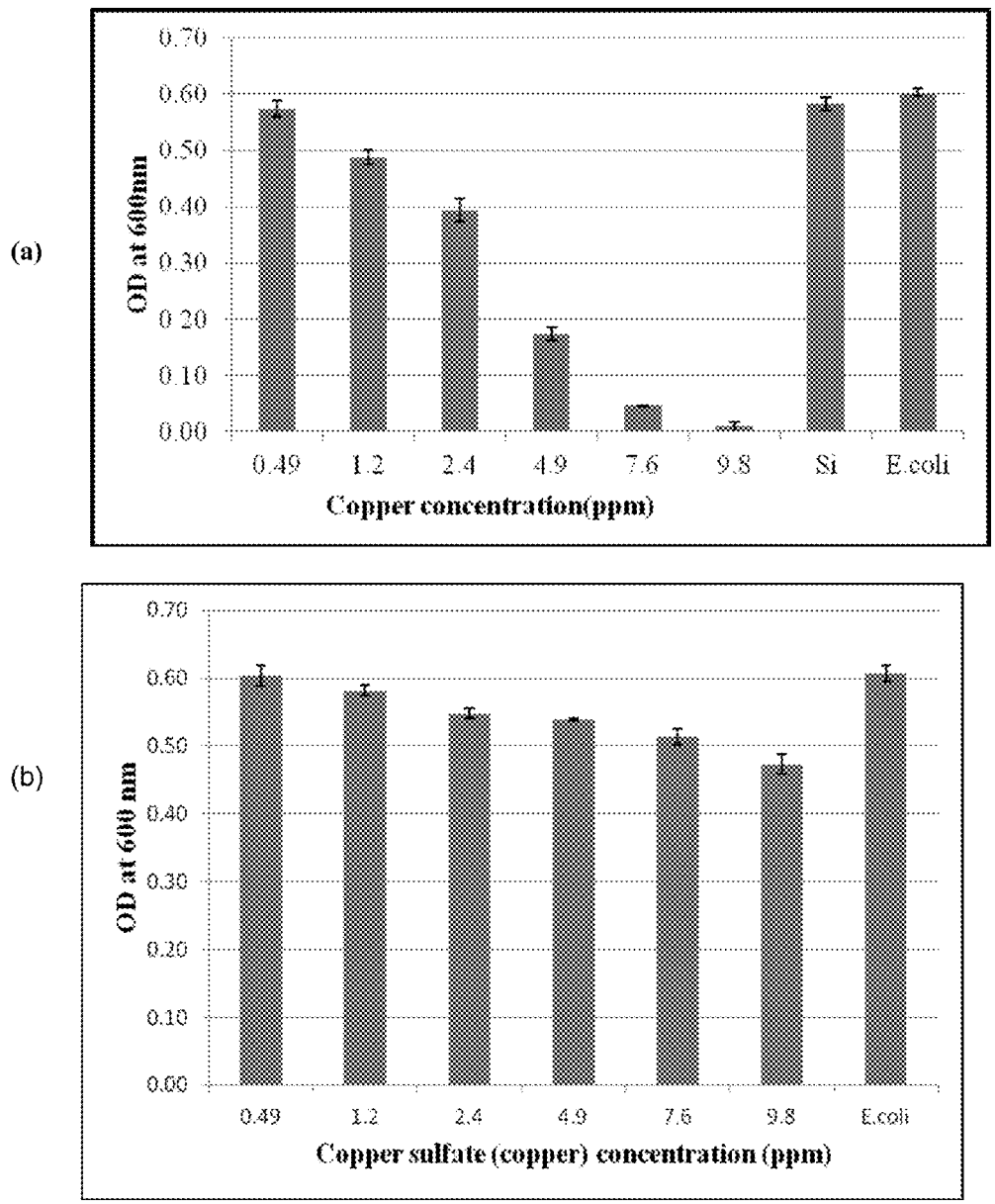
FIG. 2.3

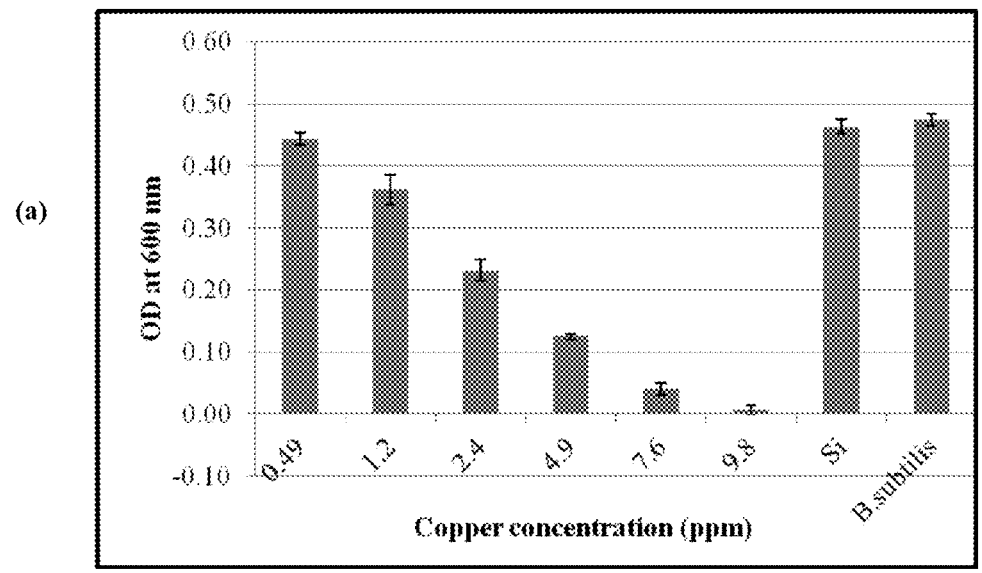
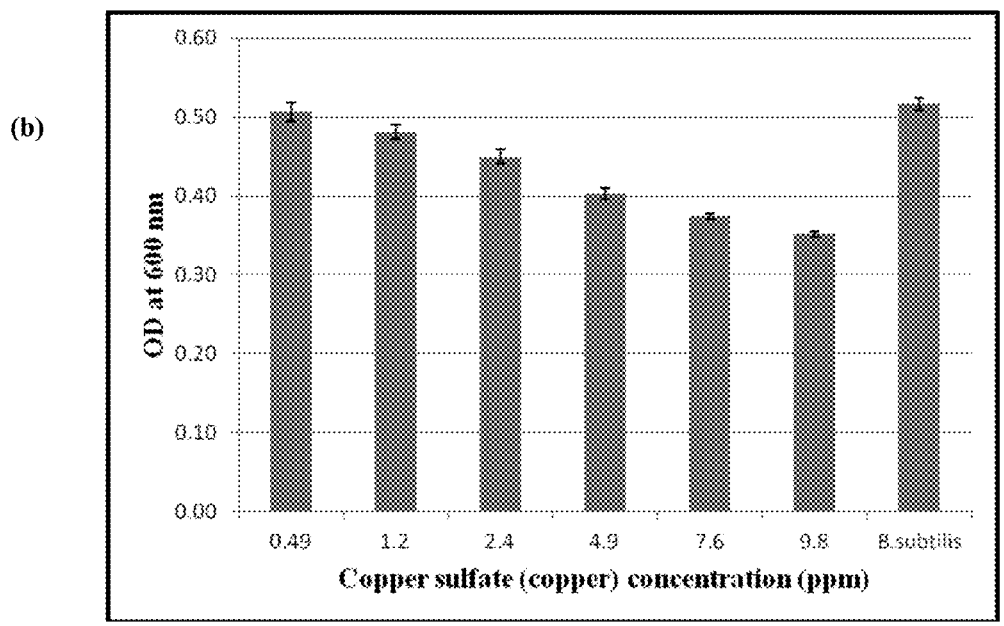
FIG. 2.4

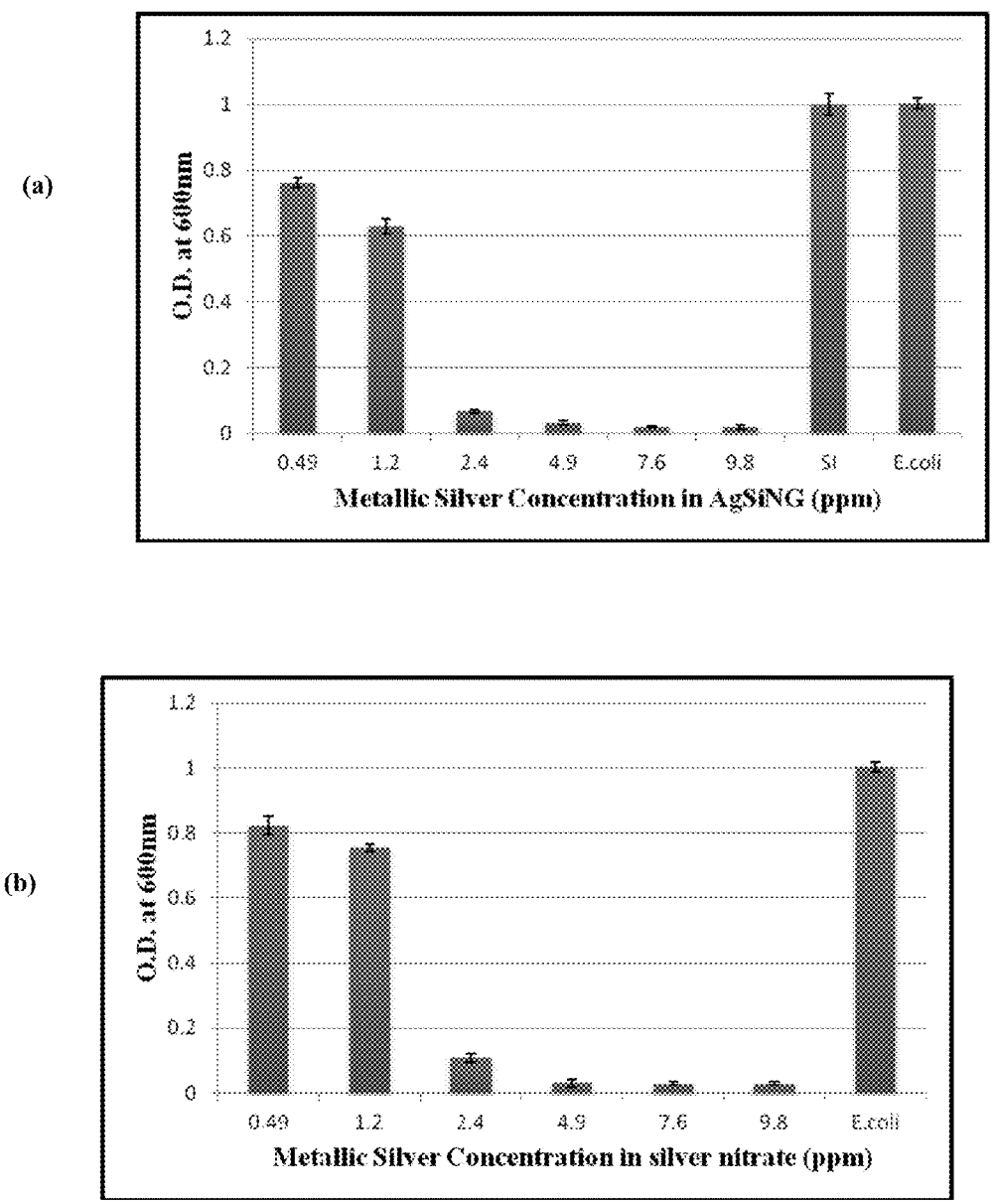
FIG. 2.5

(a) 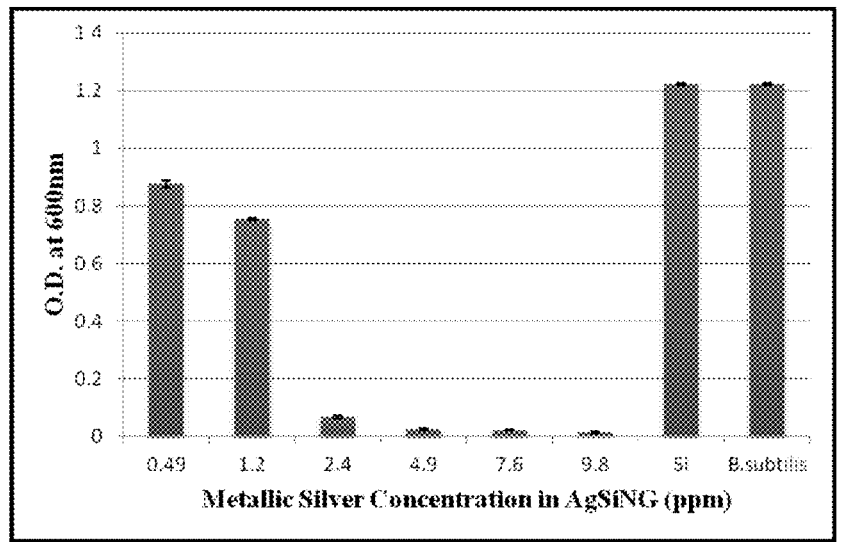
(b) 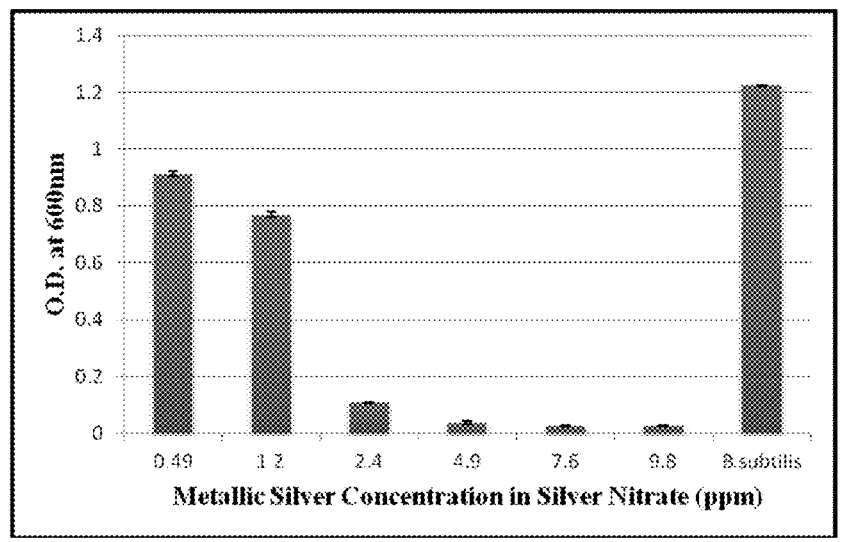
FIG. 2.6

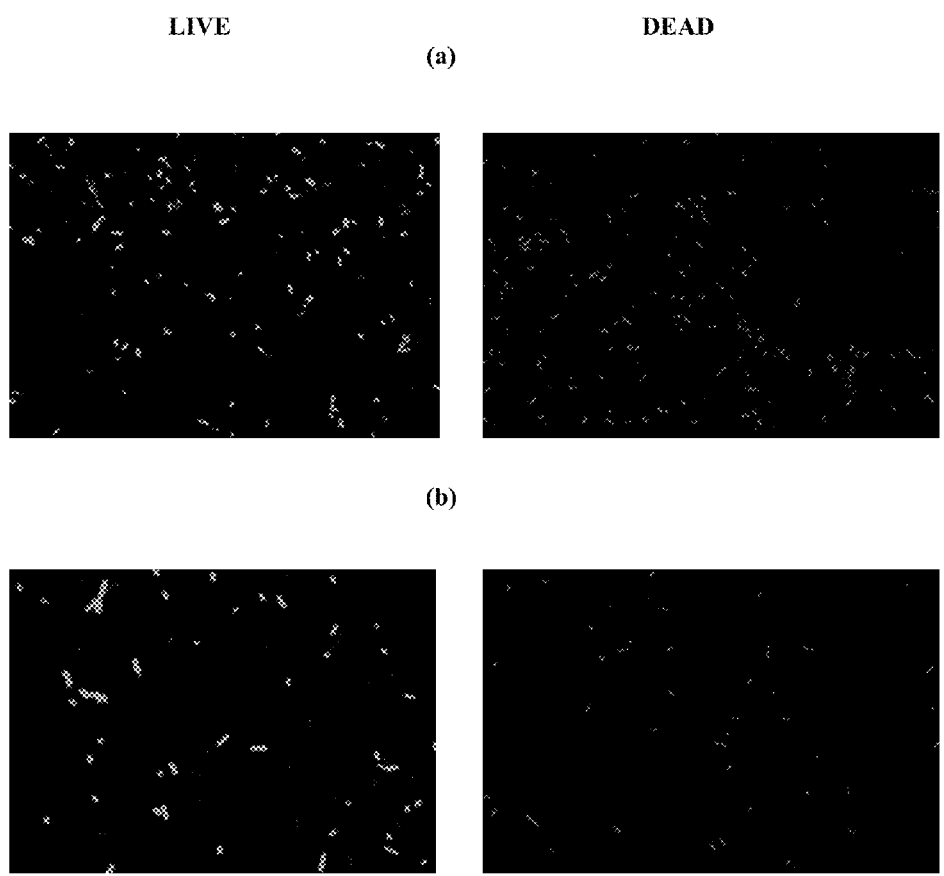
FIG. 2.7

LIVE                                    DEAD
(a)
(b)
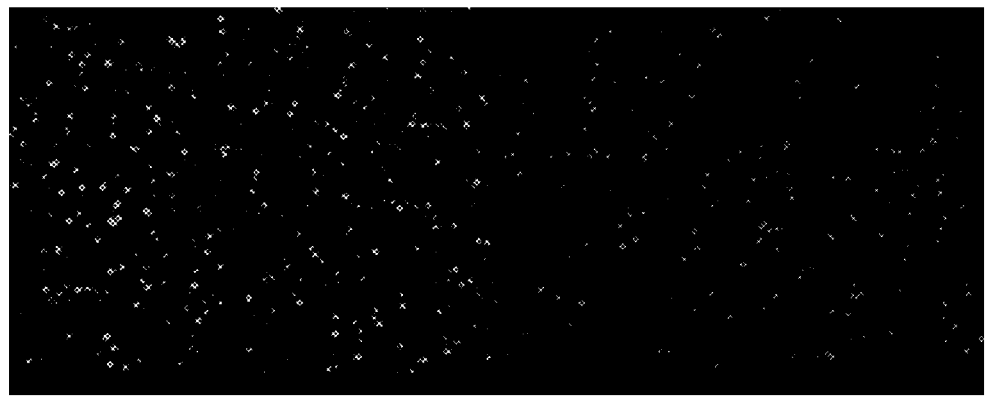
FIG. 2.8

AG LOADED SILICA NANOPARTICLE/NANOGEL FORMULATION, METHODS OF MAKING, AND METHODS OF USE

CLAIM OF PRIORITY TO RELATED APPLICATION

This application claims priority to U.S. provisional application entitled "Non-color Forming Antibacterial Ag loaded Silica Nanoparticle/nanogel Formulation" having Ser. No. 61/554,267, filed on Nov. 1, 2011, which is entirely incorporated herein by reference.

FEDERAL SPONSORSHIP

This invention was made with Government support under Contract/Grant No. 0506560, awarded by the National Science Foundation. The Government has certain rights in this invention.

BACKGROUND

Antibacterial properties of metallic silver (Ag) and Ag containing products have been known for centuries. A number of studies have shown that Ag ions posses low toxicity to human cells than microbial cells. In comparison to traditional antibiotics, Ag ions are shown to be more effective against a number of microorganisms including fungus, viruses and bacteria. This is due to the fact that these microorganisms develop low resistance against Ag ions. With this potential, silver containing compositions are very desirable for use an antibacterial agents.

SUMMARY

In accordance with the purpose(s) of the present disclosure, as embodied and broadly described herein, embodiments of the present disclosure, in one aspect, relate to compositions including a silver/silica nanocomposite, methods of making a silver/silica nanocomposite, methods of using a silver/silica nanocomposite, and the like.

In an embodiment, a composition, among others, includes: a silver/silica nanocomposite having a silica gel matrix that includes silver from one or more of silver nanoparticles or silver ions, where the silver is about 10 nanogram (ng)/mL to 100 milligram (mg)/mL of the silver/silica nanocomposite.

In an embodiment, a method of making a composition, among others, includes: mixing a silica precursor compound, a silver nanoparticle compound, and water, wherein a separate reducing agent or a separate alcohol is not added to the mixture; adjusting the pH to about 4.5 and holding for about 12 to 36 hours; adjusting the pH to about 7; and forming a silver/silica nanocomposite having a silica gel matrix that includes silver from one or more of silver nanoparticles or silver ions, where the silver is about 10 nanogram (ng)/mL to 100 milligram (mg)/mL of the silver/silica nanocomposite.

In an embodiment, a method, among others, includes: disposing a silver/silica nanocomposite on a surface, wherein the silver/silica nanocomposite includes a silica gel matrix that includes silver from one or more of silver nanoparticles and silver ions, wherein the silver is about 10 nanogram (ng)/mL to 100 milligram (mg)/mL of the silver/silica nanocomposite; and killing a substantial portion of a microorganism or inhibiting or substantially inhibiting the growth of the microorganisms on the surface of a structure or that come into contact with the surface of the surface of the structure.

Other systems, methods, features, and advantages will be, or become, apparent to one with skill in the art upon examination of the following drawings and detailed description. It is intended that all such additional structures, systems, methods, features, and advantages be included within this description, be within the scope of the present disclosure, and be protected by the accompanying claims.

BRIEF DESCRIPTION OF THE DRAWINGS

Many aspects of this disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIG. 1.1 illustrates digital images of (a) AgSiNP200 and (b) AgSiNP50 nanoformulations taken using a 12.0 megapixel Canon Powershot digital camera.

FIG. 1.2 illustrates DLS data of (a) AgSiNP200 and (b) AgSiNP50 showing average particle size (hydrodynamic diameter) and size distribution.

FIG. 1.3 illustrates SEM micrographs of (a) AgSiNP200 and (b) AgSiNP50 showing formation of Ag-silica composite particles and their aggregates.

FIG. 1.4 illustrates UV-Visible absorption spectra of (a) AgSiNP200 and (b) AgSiNP50 showing two distinct absorption peaks located at 420 nm and 300 nm in both the samples.

FIG. 1.5 illustrates HRTEM micrograph of (a) AgSiNP200 and (b) AgSiNP50 showing the formation of crystalline, nearly spherical AgNPs. The inset shows electron diffraction pattern of the AgNPs.

FIG. 1.6 illustrates well-diffusion assay performed against three different microorganisms (*E. coli, B. subtilis* and *S. aureus*) showing the formation of ZOC when wells were filled with AgSiNPs and Ag nitrate control. No ZOC was observed with the well containing SiNP control, as expected.

FIG. 1.7 illustrates the representation of *E. coli* growth (OD versus time; growth curve) in the presence of (a) AgSiNP200 and (b) AgSiNP50. Ag nitrate at the equivalent metallic Ag concentration was used as control.

FIG. 1.8 illustrates the representation of *B. subtilis* growth (OD versus time; growth curve) in the presence of (a) AgSiNP200 and (b) AgSiNP50. Ag nitrate at the equivalent metallic Ag concentration was used as control.

FIG. 1.9 illustrates the representation of *S. aureus* growth (OD versus time; growth curve) in the presence of (a) AgSiNP200 and (b) AgSiNP50. Ag nitrate at the equivalent metallic Ag concentration was used as control.

FIG. 1.10 illustrates BacLight™ fluorescence images of *E. coli* treated with (a) AgSiNP200 and (b) SiNP for 2 hours showing the presence of live (green) and dead (red) cells.

FIG. 1.11 illustrates BacLight™ fluorescence images of *B. subtilis* treated with (a) AgSiNP200 and (b) SiNP for 2 hours showing the presence of live (green) and dead (red) cells.

FIG. 1.12 illustrates BacLight™ fluorescence images of *S. aureus* treated with (a) AgSiNP200 and (b) SiNP for 2 hours showing the presence of live (green) and dead (red) cells.

FIG. 2.1 illustrates SEM images of SiNP ~380 nm (a) and C—S CuSiNP ~450 nm (b) showing particle size and morphology.

FIG. 2.2 illustrates (a) HRTEM micrograph of AgSiNG showing the presence of silver nanoparticles in amorphous silica gel and (b) HRTEM-electron diffraction pattern of silver nanoparticles present in the AgSiNG material.

FIG. 2.3 illustrates histograms showing inhibition of *E. coli* in liquid media by C—S CuSiNP (a). Silica nanoparticle was used as negative control. Copper sulfate with equivalent metallic copper concentration was used as positive control as shown in (b).

FIG. 2.4 illustrates histograms showing inhibition of *B. subtilis* in liquid media by C—S CuSiNP (a). Silica nanoparticle was used as negative control. Copper sulfate with equivalent metallic copper concentration was used as positive control as shown in (b).

FIG. 2.5 illustrates histograms showing inhibition of *E. coli* in liquid media by AgSiNG (a). Silica nanogel was used as negative control. Silver nitrate with equivalent metallic silver concentration was used as positive control as shown in (b).

FIG. 2.6 illustrate histograms showing inhibition of *B. subtilis* in liquid media by AgSiNG (a). Silica nanogel was used as negative control. Silver nitrate with equivalent metallic copper concentration was used as positive control as shown in (b).

FIG. 2.7 illustrates fluorescent microscopy images of *E. coli* (a) and *B. subtilis* (b) showing live/dead cells on treatment with C—S CuSiNP material.

FIG. 2.8 illustrates fluorescent microscopy images of *E. coli* (a) and *B. subtilis* (b) showing live/dead cells on treatment with AgSiNG material.

DETAILED DESCRIPTION

Before the present disclosure is described in greater detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features that may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, polymer chemistry, biology, and the like, which are within the skill of the art. Such techniques are explained fully in the literature.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is in atmospheres. Standard temperature and pressure are defined as 25° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

DEFINITIONS

The term "antimicrobial characteristic" refers to the ability to kill and/or inhibit the growth of microorganisms. A substance having an antimicrobial characteristic may be harmful to microorganisms (e.g., bacteria, fungi, protozoans, algae, and the like). A substance having an antimicrobial characteristic can kill the microorganism and/or prevent or substantially prevent the growth or reproduction of the microorganism.

The term "antibacterial characteristic" refers to the ability to kill and/or inhibit the growth of bacteria. A substance having an antibacterial characteristic may be harmful to bacteria. A substance having an antibacterial characteristic can kill the bacteria and/or prevent or substantially prevent the replication or reproduction of the bacteria.

The terms "alk" or "alkyl" refer to straight or branched chain hydrocarbon groups having 1 to 12 carbon atoms, preferably 1 to 8 carbon atoms, such as methyl, ethyl, n-propyl, i-propyl, n-butyl, i-butyl, t-butyl, pentyl, hexyl, heptyl, n-octyl, dodecyl, octadecyl, amyl, 2-ethylhexyl, and the like. Alkyl can include alkyl, dialkyl, trialkyl, and the like.

The terms "bacteria" or "bacterium" include, but are not limited to, Gram positive and Gram negative bacteria. Bacteria can include, but are not limited to, *Abiotrophia, Achromobacter, Acidaminococcus, Acidovorax, Acineto-* bacter, Actinobacillus, Actinobaculum, Actinomadura, Actinomyces, Aerococcus, Aeromonas, Afipia, Agrobacterium, Alcaligenes, Alloiococcus, Alteromonas, Amycolata, Amycolatopsis, Anaerobospirillum, Anabaena affinis and other cyanobacteria (including the Anabaena, Anabaenopsis, Aphanizomenon, Carnesiphon, Cylindrospermopsis, Gloeobacter Hapalosiphon, Lyngbya, Microcystis, Nodularia, Nostoc, Phormidium, Planktothrix, Pseudoanabaena, Schizothrix, Spirulina, Trichodesmium, and Umezakia genera) Anaerorhabdus, Arachnia, Arcanobacterium, Arcobacter, Arthrobacter, Atopobium, Aureobacterium, Bacteroides, Balneatrix, Bartonella, Bergeyella, Bifidobacterium, Bilophila Branhamella, Borrelia, Bordetella, Brachyspira, Brevibacillus, Brevibacterium, Brevundimonas, Brucella, Burkholderia, Buttiauxella, Butyrivibrio, Calymmatobacterium, Campylobacter, Capnocytophaga, Cardiobacterium, Catonella, Cedecea, Cellulomonas, Centipeda, Chlamydia, Chlamydophila, Chromobacterium, Chyseobacterium, Chryseomonas, Citrobacter, Clostridium, Collinsella, Comamonas, Corynebacterium, Coxiella, Cryptobacterium, Delftia, Dermabacter, Dermatophilus, Desulfomonas, Desulfovibrio, Dialister, Dichelobacter, Dolosicoccus, Dolosigranulum, Edwardsiella, Eggerthella, Ehrlichia, Eikenella, Empedobacter, Enterobacter, Enterococcus, Erwinia, Erysipelothrix, Escherichia, Eubacterium, Ewingella, Exiguobacterium, Facklamia, Filifactor, Flavimonas, Flavobacterium, Francisella, Fusobacterium, Gardnerella, Gemella, Globicatella, Gordona, Haemophilus, Hafnia, Helicobacter, Helococcus, Holdemania Ignavigranum, Johnsonella, Kingella, Klebsiella, Kocuria, Koserella, Kurthia, Kytococcus, Lactobacillus, Lactococcus, Lautropia, Leclercia, Legionella, Leminorella, Leptospira, Leptotrichia, Leuconostoc, Listeria, Listonella, Megasphaera, Methylobacterium, Microbacterium, Micrococcus, Mitsuokella, Mobiluncus, Moellerella, Moraxella, Morganella, Mycobacterium, Mycoplasma, Myroides, Neisseria, Nocardia, Nocardiopsis, Ochrobactrum, Oeskovia, Oligella, Orientia, Paenibacillus, Pantoea, Parachlamydia, Pasteurella, Pediococcus, Peptococcus, Peptostreptococcus, Photobacterium, Photorhabdus, Phytoplasma, Plesiomonas, Porphyrimonas, Prevotella, Propionibacterium, Proteus, Providencia, Pseudomonas, Pseudonocardia, Pseudoramibacter, Psychrobacter, Rahnella, Ralstonia, Rhodococcus, Rickettsia Rochalimaea Roseomonas, Rothia, Ruminococcus, Salmonella, Selenomonas, Serpulina, Serratia, Shewenella, Shigella, Simkania, Slackia, Sphingobacterium, Sphingomonas, Spirillum, Spiroplasma, Staphylococcus, Stenotrophomonas, Stomatococcus, Streptobacillus, Streptococcus, Streptomyces, Succinivibrio, Sutterella, Suttonella, Tatumella, Tissierella, Trabulsiella, Treponema, Tropheryma, Tsakamurella, Turicella, Ureaplasma, Vagococcus, Veillonella, Vibrio, Weeksella, Wolinella, Xanthomonas, Xenorhabdus, Yersinia, and Yokenella. Other examples of bacterium include Mycobacterium tuberculosis, M. bovis, M. typhimurium, M. bovis strain BCG, BCG substrains, M. avium, M. intracellulare, M. africanum, M. kansasii, M. marinum, M. ulcerans, M. avium subspecies paratuberculosis, Staphylococcus aureus, Staphylococcus epidermidis, Staphylococcus equi, Streptococcus pyogenes, Streptococcus agalactiae, Listeria monocytogenes, Listeria ivanovii, Bacillus anthracis, B. subtilis, Nocardia asteroides, and other Nocardia species, Streptococcus viridans group, Peptococcus species, Peptostreptococcus species, Actinomyces israelii and other Actinomyces species, and Propionibacterium acnes, Clostridium tetani, Clostridium botulinum, other Clostridium species, Pseudomonas aeruginosa, other Pseudomonas species, Campylobacter species, Vibrio cholera, Ehrlichia species, Actinobacillus pleuropneumoniae, Pasteurella haemolytica, Pasteurella multocida, other Pasteurella species, Legionella pneumophila, other Legionella species, Salmonella typhi, other Salmonella species, Shigella species Brucella abortus, other Brucella species, Chlamydi trachomatis, Chlamydia psittaci, Coxiella burnetti, Escherichia coli, Neiserria meningitidis, Neiserria gonorrhea, Haemophilus influenzae, Haemophilus ducreyi, other Hemophilus species, Yersinia pestis, Yersinia enterolitica, other Yersinia species, Escherichia coli, E. hirae and other Escherichia species, as well as other Enterobacteria, Brucella abortus and other Brucella species, Burkholderia cepacia, Burkholderia pseudomallei, Francisella tularensis, Bacteroides fragilis, Fudobascterium nucleatum, Provetella species, and Cowdria ruminantium, or any strain or variant thereof. The Gram-positive bacteria may include, but is not limited to, Gram positive Cocci (e.g., Streptococcus, Staphylococcus, and Enterococcus). The Gram-negative bacteria may include, but is not limited to, Gram negative rods (e.g., Bacteroidaceae, Enterobacteriaceae, Vibrionaceae, Pasteurellae and Pseudomonadaceae). In an embodiment, the bacteria can include Mycoplasma pneumoniae.

The term "protozoan" as used herein includes, without limitations flagellates (e.g., Giardia lamblia), amoeboids (e.g., Entamoeba histolitica), and sporozoans (e.g., Plasmodium knowlesi) as well as ciliates (e.g., B. coli). Protozoan can include, but it is not limited to, Entamoeba coli, Entamoeabe histolitica, Iodoamoeba buetschlii, Chilomastix meslini, Trichomonas vaginalis, Pentatrichomonas homini, Plasmodium vivax, Leishmania braziliensis, Trypanosoma cruzi, Trypanosoma brucei, and Myxoporidia.

The term "algae" as used herein includes, without limitations microalgae and filamentous algae such as Anacystis nidulans, Scenedesmus sp., Chlamydomonas sp., Clorella sp., Dunaliella sp., Euglena so., Prymnesium sp., Porphyridium sp., Synechoccus sp., Botryococcus braunii, Crypthecodinium cohnii, Cylindrotheca sp., Microcystis sp., Nochrysis sp., Monallanthus salina, minutum, Nannochloris sp., Nannochloropsis sp., Neochioris oleoabundans, Niizschia sp., Phaeodactylum tricornutum, Schizochytrium sp., Senedesmus obliquus, and Tetraselmis sucica as well as algae belonging to any of Spirogyra, Cladophora, Vaucheria, Pithophora and Enteromorpha genera.

The term "fungi" as used herein includes, without limitations, a plurality of organisms such as molds, mildews and rusts and include species in the Penicillium, Aspergillus, Acremonium, Cladosporium, Fusarium, Mucor, Nerospora, Rhizopus, Tricophyton, Botryotinia, Phytophthora, Ophiostoma, Magnaporthe, Stachybotrys and Uredinalis genera.

Discussion:

In accordance with the purpose(s) of the present disclosure, as embodied and broadly described herein, embodiments of the present disclosure, in one aspect, relate to compositions including a silver/silica nanocomposite, methods of making a silver/silica nanocomposite, methods of using a silver/silica nanocomposite, and the like. In an embodiment, the composition can be used as an antimicrobial agent to kill and/or inhibit the formation of microorganisms on a surface. An advantage of the present disclosure is that the composition is substantially (e.g., greater than about 95% and about 99%) or completely transparent to visible light unlike other compositions using silver which cause a discoloration of the surface.

In an embodiment, the composition that includes the silver/silica nanocomposite may have an antimicrobial characteristic (e.g., kills at least 70%, at least 80%, at least 90%, at least 95%, or at least 99% of the microorganisms (e.g., bacteria) on the surface and/or reduces the amount of microorganisms that form or grow on the surface by at least 70%, at least 80%, at least 90%, at least 95%, or at least 99%, as compared to a similar surface without the composition disposed on the surface). Additional details are described in the Examples.

In an embodiment, the composition can be disposed on a surface of a structure. In an embodiment, the structure can include those that may be exposed to microorganisms and/or that microorganisms can grow on such as, without limitation, fabrics, cooking counters, food processing facilities, kitchen utensils, food packaging, swimming pools, metals, drug vials, medical instruments, medical implants, yarns, fibers, gloves, furniture, plastic devices, toys, diapers, leather, tiles, and flooring materials. In an embodiment, the structure can include textile articles, fibers, filters or filtration units (e.g., HEPA for air and water), packaging materials (e.g., food, meat, poultry, and the like food packaging materials), plastic structures (e.g., made of a polymer or a polymer blend), glass or glass like structures on the surface of the structure, metals, metal alloys, or metal oxides structure, a structure (e.g., tile, stone, ceramic, marble, granite, or the like), and a combination thereof.

As mentioned above, the composition includes a silver/silica nanocomposite. In an embodiment, the silver/silica nanocomposite includes a silica gel matrix that includes silver as silver ions and silver nanoparticles. In an embodiment, the silver can be about 10 nanogram (ng)/mL to 100 milligram (mg)/mL or about 100 ng/mL to 10 microgram (µg)/mL weight percent, of the silver/silica nanocomposite.

"Silica gel matrix" or "silica nanogel matix" refers to amorphous gel like substance that is formed by the interconnection of silica particles (e.g., nanoparticles (e.g., 2 to 500 nm or 5 to 50 nm)) to one another. In an embodiment, the amorphous silica gel has no ordered (e.g., defined) structure (opposite to crystalline structure) so an "amorphous gel" refers to gel material having amorphous structural composition. In an embodiment, the silica nanoparticles of the silica gel are interconnected covalently (e.g., through —Si—O—Si— bonds), physically associated via Van der Waal forces, and/or through ionic interactions (e.g., with silver ions).

In an embodiment, the silica particles are interconnected and silver nanoparticles can be disposed within the silica gel matrix and/or attached to one or more silica particles. In an embodiment, the silver nanoparticles are substantially (e.g., greater than about 80%, about 90%, about 95%, or about 99%) monodisperse. In an embodiment, the silica gel is disposed around the entire silver nanoparticle, which, although not intending to be bound by theory, causes the silver/silica nanocomposite to be transparent to visible light. Embodiments of the present disclosure include the appropriate ratio of silica gel to silver nanoparticle so that the nanocomposite is transparent to visible light while also maintaining antimicrobial characteristics. Unlike other silver compositions, embodiments of the present disclosure have the advantage of not discoloring the surface it is disposed on since it is transparent to visible light.

In an embodiment, the diameter of the particles (e.g., silica and/or silver) can be varied from a few nanometers to hundreds of nanometers by appropriately adjusting synthesis parameters, such as amounts of silane precursor, polarity of reaction medium, pH, time or reaction, and the like. For example, the diameter of the particles can be controlled by adjusting the time frame of the reaction. In an embodiment, the silica and silver nanoparticles can independently be about 2 to 25 nm or about 5 to 20 nm. In addition, the concentration of the silver ions can be by appropriately adjusting synthesis parameters, such as amounts of silane precursor, polarity of reaction medium, pH, time or reaction, and the like.

In an embodiment, the silver ions can interact with the silica in one or more ways. For example, weak interactions of $Ag^+$ ions with silica (Si—OH or $SiO^-$), forming Si—O—Ag (covalent) or Si—$O^-Ag^+$ (electrostatic) may be present in the silver/silica nanocomposite. In another example, the $Ag^+$/silica interaction can result in the formation of [—Si—OH$\Longrightarrow$$Ag^+$$\Longleftarrow$HO—Si—], i.e., formation of coordinate covalent bond where the lone pair of oxygen atom participates in the bond formation, much like $[Ag(NH_3)_2]^+$-silver ammonium complex.

In an embodiment, a silica precursor material to make the silver silica nanocomposite can be made by mixing a silane compound (e.g., alkyl silane, tetraethoxysilane (TEOS), tetramethoxysilane, sodium silicate, or a silane precursor that can produce silicic acid or silicic acid like intermediates and a combination of these silane compounds) with a silver nanoparticle precursor compound (e.g. silver nitrate salt, a silver chelate (e.g., chelating agent such p-dimethylaminobenzalrhodanine, tris(phenanthroline)Fe(II), and thiol silver complexing chelates (mercaptans such as dimethylsulfoniopropanoate, mercaptomethane, and the like)), and a combination thereof) in an acidic medium (e.g., acidic water). In an embodiment, the pH can be adjusted to about 4.5 using an acid such as nitric acid. In an embodiment, the weight ratio of the silica precursor material to the silver precursor material can be about 1:1 to 30:1 or about 4:1 to 15:1. After mixing for a period of time (e.g., about 30 minutes to a few hours or about 12 to 36 hours), a mixture including silica nanoparticles with the silver nanoparticles can be formed. Subsequently, the medium can be brought to a pH of about 7 and held for a time period (e.g., a few hours to a day) to form a silica nanoparticle gel, where the silica nanoparticles are interconnected. In an embodiment, the silver nanoparticles can be part of the interconnection of the silica nanoparticles and/or dispersed within the matrix. This process can be performed using a single reaction vessel or can use multiple reaction vessels. In an embodiment, a separate reducing agent or alcohol in not needed to form the silver nanoparticles, which simplifies the reaction and reduces cost.

In an embodiment, after the composition is disposed on the surface, the structure may have an antimicrobial characteristic that is capable of killing a substantial portion of the microorganisms (e.g., bacteria such as *E. coli, B. subtilis* and *S. aureus*) on the surface of the structure and/or inhibits or substantially inhibits the growth of the microorganisms on the surface of the structure. The phrase "killing a substantial portion" includes killing at least about 70%, at least about 80%, at least about 90%, at least about 95%, or at least about 99% of the microorganism (e.g., bacteria) on the surface that the composition is disposed on, relative to structure that does not have the composition disposed thereon. The phrase "substantially inhibits the growth" includes reducing the growth of the microorganism (e.g., bacteria) by at least about 70%, at least about 80%, at least about 90%, at least about 95%, or at least about 99% of the microorganisms on the surface that the composition is disposed on, relative to a structure that does not have the composition disposed thereon.

EXAMPLES

Example I

Brief Introduction

Silver nanoparticles (AgNPs) are considered a highly potent antibacterial agent and they are superior to commonly used disinfectants such as sodium hypochlorite and phenol. Due to outstanding antibacterial properties, there is an increasing demand of incorporating AgNPs into consumer products to achieve strong antimicrobial properties. To date, hundreds of consumer products including antimicrobial fabrics, deodorizer, cosmetic and pet products are available in the market, which uses antimicrobial AgNPs. Efficient loading of AgNPs as well as active silver ions within a delivery matrix is important for prolonged antimicrobial efficacy. In this example, we report preparation of a stable formulation of Ag-silica composite nanoparticles (AgSiNPs) co-loaded with both AgNPs and Ag ions. A simple sol-gel mediated method was used to prepare the nanomaterial. Co-loading of AgNPs and Ag ions was confirmed by characteristic UV-Vis spectroscopic data. Average particle size and size distribution of the AgSiNP materials were estimated by the High-Resolution Transmission Electron Microscopy (HRTEM), Dynamic Light Scattering (DLS) and the Scanning Electron Microscopy (SEM). The antimicrobial property of the AgSiNP formulations was tested against Gram-negative (*E. coli*) and Gram-positive (*B. subtilis, S. aureus*) bacteria. It was observed that the antibacterial properties of silver remained intact upon loading in silica matrix. Silica being an environmentally-friendly material, the present AgSiNP material could be incorporated into spray based formula for "touch-safe" antimicrobial surface coating applications.

Introduction

Antibacterial properties of metallic silver (Ag) and Ag containing products have been known for centuries[1,2]. A number of studies have shown that Ag ions posses low toxicity to human cells than microbial cells[3,4]. In comparison to traditional antibiotics, Ag ions are shown to be more effective against a number of microorganisms including fungus, viruses and bacteria. This is due to the fact that these microorganisms develop low resistance against Ag ions[5]. Moreover, Ag has outstanding thermal stability[4]. Due to all these attractive properties, Ag based antimicrobials have been widely applied in a large number of consumer products including molded plastic products, textiles, air filters and water purifiers[6]. Ag containing spray formula has been used in food processing and sanitation facilities. Despite all these applications, the inhibitory effect of silver in controlling bacterial growth has not been fully understood. Feng et al. has shown that Ag ions interact with DNA, impairing the DNA replication process[7]. They have also shown that Ag ions effectively bind to thiols of proteins inhibiting their functional activity.[7,8]

It is desirable to load Ag in a stable preferable inorganic based delivery matrix such as silica. This is important for applications where chemical and thermal stability of the material is demanded. For certain thermoplastic based products requiring high-temperature (>300° C.) processing[9], organic polymeric materials such as poly(L-lactide) fibers loaded with Ag ions[10] may experience some limitations[11]. Silica based Ag delivery system could serve as an attractive alternative to organic polymers. This is due to the fact that silica is a chemically inert material and it exhibits outstanding thermal stability[12]. Moreover, silica matrix is considered as biocompatible and environmentally-friendly material.

Due to simplicity, sol-gel method has been popularly used to prepare Ag-silica nanocomposites[13-19]. This method usually involves hydrolysis and condensation of a silane reagent (such as tetraethylorthosilicate, TEOS) in water-ethanol mixture in presence of an acid or a base catalyst and a suitable Ag precursor (usually Ag salts or Ag-chelates). Two different strategies of making Ag-silica nanocomposites have been reported in the literature. In one strategy, Ag salts were reduced to deposit Ag nanoparticles (AgNPs) over the pre-formed silica particles[18]. In another strategy, Ag-silica nanocomposite material is prepared where Ag is loaded throughout the silica matrix[13-19]. Since Ag is the active agent, improved antibacterial efficacy is expected from the former Ag-silica nanocomposite[18] due to increased bioavailability of the Ag ions from the surface-adhered AgNPs. However, the Ag-silica nanocomposite prepared using the later strategy should exhibit slow release of Ag ions from the silica matrix and therefore could show a sustained antibacterial efficacy. Therefore, antibacterial properties of Ag loaded silica nanocomposites have been mostly evaluated[15, 16, 20-24].

Despite the simplicity of the sol-gel method of making Ag-silica nanocomposites, there are significant differences in the literature reported synthesis procedures. To prepare AgNPs, most of the synthesis techniques use a reducing agent to reduce Ag ions to metallic Ag[25-31]. In a typical sol-gel synthesis procedure, ethanol is used along with other components including a silica precursor (such as TEOS) and a catalyst (acid or a base)[32, 33]. In some cases, the synthesis procedure involves heating of the reaction mixture or sonication[30, 34-36]. It is shown in the literature that reaction conditions greatly influence AgNP crystallinity, size and shape[37]. Therefore, it becomes quite challenging to correlate antibacterial efficacy of the Ag-silica nanocomposites with respect to different forms of Ag (ionic Ag, Ag clusters, AgNPs). To the best of our knowledge, no systematic antibacterial studies have been reported on the Ag-silica nanocomposite materials where Ag is loaded in the silica matrix in both ionic and AgNP forms.

Ionic Ag and AgNPs are the active antibacterial species in Ag-silica nanocomposite material. It is believed that the AgNPs are more potent than the ionic Ag species although AgNPs releases Ag ions in the aqueous solution[18, 21]. The mechanism of antibacterial activity of Ag in its ionic and NP forms is not yet fully understood. A general consensus is that Ag ions damages bacterial cell walls[7, 38]. AgNPs can cause severe damage to cell walls by strongly interacting with the bacterial cells. They can even penetrate through the cell wall and populate in the intra-cellular regions[23, 38]. It would be therefore interesting to study antibacterial properties of Ag-silica nanocomposites where Ag is loaded in silica matrix both in its ionic and NP forms. Also, it would be interesting to evaluate the antibacterial efficacy with respect to metallic Ag loading.

In this example, we report synthesis of Ag-silica nanocomposites co-loaded with Ag in both ionic and NP forms using an acid-catalyzed sol-gel method. Unlike any other synthesis methods, the present method uses no reducing agent or alcohol for producing AgNPs. Again, this is a simple one-pot room-temperature synthesis method that does not involve any heating or sonication. The present method produces colloidal suspension of Ag-silica composite particles in DI water that requires no purification process prior to antibacterial studies. The resulting Ag-silica aqueous formula is completely transparent and stable for months at neutral pH condition, making it attractive for potential use as "touch-safe" antimicrobial spray-based applications.

Materials and Methods

All the reagents used to synthesize Ag loaded SiNPs were procured from commercial vendors and they were used without further purification. Two different Ag loaded SiNP formulations were prepared (AgSiNP200 and AgSiNP50). The AgSiNP200 formula was prepared by mixing 120 mg of Ag nitrate salt 99.5%, analytical grade (Acros Organics), 600 μl of TEOS (Fisher Scientific; Fair Lawn, N.J., USA) in 100 mL DI water (Nanopure; Barnstead Model # D11911) under continuous magnetic stirring at 400 rpm. The pH of this reaction mixture was adjusted to 4.5 by adding dropwise 1M nitric acid (Fisher Scientific) stock solution in DI water. After 24 hrs, the pH of the reaction mixture was further adjusted to 7.0 by dropwise adding 2.0 mM NaOH (Fisher Scientific), stock solution. The AgSiNP50 formula was similar to the AgSiNP200 except that the amount of Ag nitrate added was 34 mg. Ag nitrate solution in DI water was used as a positive control and SiNP (without Ag, prepared using the above mentioned procedure) was used as negative control for all antibacterial studies. The AgSiNP materials in both these formulations were highly soluble. Because of high solubility, the AgSiNP material could not be centrifuged down from the solution. Lyophilized AgSiNP material could not be re-dispersed in DI water. An attempt to purify the AgSiNP material using dialysis technique was not efficient and reliable. No significant change in ionic Ag content before and after the dialysis was observed (as measured by the UV-Vis spectroscopy). Due to these limitations, the AgSiNP nanoformulations were directly used for characterization and antibacterial studies without any purification. Metallic Ag loading in AgSiNP material was estimated by lyophilizing the samples and measuring the dry weight of the resulting yellowish powder material. Metallic Ag content per mg of powder sample was 0.24 mg (24.19 wt %) for AgSiNP200 and 0.105 mg (10.59 wt %) for AgSiNP50.

Material Characterization

Hydrodynamic (HD) size of both AgSiNP200 and AgSiNP50 materials was estimated using Dynamic Light Scattering (DLS) using Precision Detector/Cool batch 4T DLS instrument with the assumption that the AgSiNPs are spherical/semispherical in shape[39]. Scanning Electron Microscopy (SEM, Zeiss ULTRA-55 FEG) and High-Resolution Transmission Electron Microscopy (HRTEM, FEI Tecnai F30) were used to characterize particle size as well as the morphology of the AgSiNPs. SEM samples were prepared by spin coating 20 microliters of the AgSiNPs in DI water on a silicon wafer. Samples for the HRTEM were prepared by placing a drop of the AgSiNPs in DI water on a carbon-coated copper grid (400 mesh) followed by drying under vacuum for overnight. UV-Vis spectra of the AgSiNP200 and AgSiNP50 materials were recorded using Cary 300 bio UV-Visible Spectrophotometer. Baseline corrections were done using SiNP control.

Antibacterial Assays

Antibacterial properties of AgSiNP200 and AgSiNP50 were evaluated against Gram-positive, *Bacillus subtilis* (*B. subtilis*, ATCC 9372) and *Staphylococcus aureus* (*S. aureus*, ATTC 25923) and a Gram-negative, *Escherichia coli* (*E. coli*, ATCC 35218) organism. Ag nitrate was used as positive control and the SiNP (without silver) was used as negative control. In all Ag containing test materials (including the positive control), the metallic Ag concentration was kept identical with the consideration that Ag is the active antibacterial agent. All the bacteria were obtained from the UCF Department of Molecular Biology and Microbiology Preparatory Laboratories) by Microbiology Department, University of Central Florida, Orlando. All the antibacterial assays were done using Mueller Hinton II medium (Fulka Analytical, USA).

The well diffusion method was used to evaluate the antibacterial efficacy of the AgSiNPs following a published literature procedure[40]. The procedure is briefly described below. First, $10^8$ CFU/ml of bacteria was spread-plated on Mueller Hinton agar II plates aseptically. In the next step, five 3 mm sized wells were prepared aseptically. These wells were then filled with 10 μl of the test materials and controls (AgSiNP200, AgSiNP50, two Ag nitrate controls, $AgNO_3200$ and $AgNO_350$ with equivalent Ag concentration as in the AgSiNP200 and AgSiNP50 materials respectively and SiNP). The plates were incubated at 36° C. for 24 hours. The zone of clearance (ZOC) was observed after 24 hours of growth.

The bacterial inhibition studies for the AgSiNP200 and AgSiNP50 were done using a method as described by Rastogi et al.[41]. The procedure is briefly described below. Different concentrations of AgSiNP200 (metallic silver concentrations of 63.5 μg/ml, 38.1 μg/ml, 19.05 μg/ml, 9.53 μg/ml, 4.77 μg/ml, 2.68 μg/ml, 1.34 μg/ml, 953 ng/ml, 477 ng/ml, 95.3 ng/ml and 47.7 ng/ml) and AgSiNP50 (metallic silver concentrations of 30.24 μg/ml, 20.16 μg/ml, 10.08 μg/ml, 5.04 μg/ml, 2.52 μg/ml, 1.26 μg/ml, 630 ng/ml and 63 ng/ml) were prepared in sterile Mueller Hinton II broth in sterile tubes. To achieve uniform growth for this comparative study, all the tubes contained same amount of broth. We have used 0.85% of sterile saline to make up the volume to 0.9 ml in each tube. In the next step, 0.1 ml of $10^6$ CFU/ml of bacteria culture was added to each tube. Appropriate amount of saline and Mueller Hilton II broth were combined to prepare the blank containing only 0.1 ml of $10^6$ CFU/ml of bacteria culture. The turbidity (optical density, OD) of the solution indicative the bacterial growth was recorded using a visible spectrophotometer (Teysche 800) at 600 nm wavelength. The OD values were recorded every hour for the duration of nine hours. Initial OD reading at time zero was considered as blank. The final OD reading was also recorded after completion of 24 hour incubation. The growth curve was generated by plotting the OD values against time (in hours) each bacterial species.

The live/dead cell viability assay was performed on all the Ag containing test materials using the BacLight™ bacterial viability kit L7012[41] (Invitrogen, USA). In a typical procedure, test samples were incubated with bacteria ($10^5$ cells/mL of sample) for 2 hours at 36° C. on 150 rpm shaker. Bacterial cells were then centrifuged 10,000 rpm for 10 min, the supernatant was discarded and the cells were re-suspended in 0.85% saline. These steps were repeated for two times to achieve thorough washing. Next, the bacterial pellet was re-suspended in 1.0 of 0.85% sterile saline followed by the addition of 3 μL of the BacLight™ dye mixture (as per the company protocol). The resulting mixture was incubated at the room temperature in dark condition for 15 minutes. Next, 5 μL of the labeled bacterial suspension stained was placed on a sterile glass slide and then covered with a sterile coverslip. Slides were then placed under a fluorescence microscope (Ziess LSM 780) for imaging samples.

Results and Discussion

The AgSiNP200 formula developed pale yellow color (FIG. 1.1a) after the pH adjustment to 7.0 but very faint yellow coloration was visually observed for the AgSiNP50formula (FIG. 1.1b). It is noted that both nanoformulations were completely transparent before and after the pH adjustment. The development of yellow color is indicative of AgNP formation as reported by others[29].

Dynamic light scattering (DLS) measurements of AgSiNP200 and AgSiNP50 in DI water show the formation of particulate matters. The HD size was estimated to be 191 nm and 111 nm AgSiNP200 and AgSiNP50, respectively. Representative DLS data have been presented in FIG. 1.2. The SEM micrographs (FIG. 1.3) show the formation of NPs with average size of 35 and 40 nm in both the AgSiNP200 and AgSiNP50 samples (estimated by considering 100 particles and individually measuring the particle size using the ImageJ image processing software[42]). Particles appeared to be fairly monodispersed except some discrete aggregations of nanoparticles were observed in both samples. Broad distribution of particle size as observed in the DLS data also supports the formation of particle aggregates and correlates the SEM results.

The UV-Vis absorption spectra of both the AgSiNP200 and AgSiNP50 show two distinct absorption bands located around 295 nm and 420 nm. FIG. 1.4a and FIG. 1.4b show the corresponding UV-Vis spectra of the AgSiNP200 and AgSiNP50, respectively. The peak at ~295 nm is assigned to silica-Ag ion complex or Ag ion clusters embedded in silica matrix. Similar observation was reported by Li et al. where the appearance of the 295 nm was assigned to Ag cluster formation[43]. The appearance UV-Vis peak at 420 nm is due to surface plasmon resonance (SPR) absorption of AgNPs[44, 45]. The UV-Vis spectra suggested the presence of both ionic Ag and AgNPs in the silica matrix.

HRTEM images of AgSiNP200 and AgSiNP50 are shown in FIG. 1.5a and FIG. 1.5b, respectively. Formation of nearly spherical and crystalline AgNPs in the size range approximately between 5 nm and 20 nm is confirmed from these images. The HRTEM-Selected Area Electron Diffraction (SAED) pattern as shown in the inset of FIG. 1.5a and FIG. 1.5b confirmed further crystalline structure of the AgNPs. However, a careful investigation reveals that AgNPs were primarily polycrystalline and there are amorphous regions within most of the AgNPs (as pointed with an arrow-head). Amorphous silica matrix around the crystalline AgNPs could not be clearly imaged due to low density.

The mechanism of the formation of AgNPs is not well understood. Since no external reducing agent was added to the reaction mixture during the AgSiNP synthesis, it is suggested that silica[46] (at neutral pH) and ethanol (the by-product of TEOS hydrolysis) have served as mild reducing agents for partly converting Ag ions to metallic Ag. It is possible that the crystalline material is a combination of metallic AgNPs and Ag oxide NPs. However, the oxidation states of crystalline AgNP structures could not be reliably measured using the HRTEM or the X-ray Photo Electron Spectroscopy.

Silver ions can bind with the silica hydroxyl groups, forming the Si—O—Ag bond. Such interaction of silver ions with silica will limit condensation reaction of silicic acid which is formed upon TEOS hydrolysis[47]. This could restrict three-dimensional growth of silica network and prevent the gelation process. The Ag silica nanocomposite material is stable for months at the room temperature and no significant change in the particle size is observed by the DLS over time. Because of Si—O—Ag bond formation, it is expected that the release of free Ag ions from the material will be restricted, leading to sustained antibacterial property.

Antibacterial Efficacy of AgSiNP Formulation

The antibacterial efficacy of AgSiNP aqueous formulation was tested against *E. coli, B. subtilis* and *S. aureus* using a number of assays including well-diffusion assay, cell viability assay and assay for the inhibition of cell growth. We have performed antibacterial efficacy testing of the AgSiNP formulations using traditional disc-diffusion assay (DDA). Cellulose discs used in this assay were completely soaked with AgSiNP formulation and air-dried prior to placing them on agar plates. There was no ZOC observed in DDA confirming strong adherence of the AgSiNP material to the cellulose discs[48] (data not shown). The absence of the ZOC also confirms that there is no significant release of Ag ions from the AgSiNP containing discs. The DDA however showed ZOC for the Ag nitrate control, confirming Ag ion release. To avoid the limitation of the above DDA, we have performed well-diffusion assay (the details of this assay is described in the Materials and Methods section). The well-diffusion assay showed zone of clearance (ZOC, outer diameter of the clear zone ~9±1 mm; FIG. 1.6) around the wells containing the AgSiNP treatments and Ag nitrate controls. The results confirm that the active agent, Ag (Ag ions and AgNPs) can diffuse from the well to the surrounding agar. There is however no significant difference in the ZOC value between the AgSiNP material and the Ag nitrate control. There was no ZOC around the well containing SiNP formulation (FIG. 1.6) which suggests that SiNP does not have any noticeable anti-bacterial property.

The growth inhibition assay is based on turbidity of the solution containing bacteria. The turbidity of the solution is measured by measuring the optical density (OD) at 600 nm. If there is a bacterial growth, the OD value will increase over time. The growth inhibition assay was performed against *E. coli, B. subtilis* and *S. aureus* and the results are shown in FIG. 1.7, FIG. 1.8 and FIG. 1.9, respectively. At 2.68 ppm metallic Ag concentration, nearly complete inhibition of growth (OD value <0.1) of all three types of microorganisms was observed for the AgSiNP200 nanoformulation. The AgSiNP50 nanoformulation exhibited very similar results where nearly complete inhibition of bacterial growth was observed at 2.52 ppm of metallic silver concentration. There is no significant difference in growth inhibition results obtained for the Ag nitrate control, suggesting that silica matrix did not compromise the overall antibacterial efficacy of the active agent, Ag. As expected, SiNP formulation did not inhibit bacterial growth.

The Live/Dead® BacLight™ bacterial viability kit was used for the assessment of bacterial viability, indicative of the bactericidal efficacy of the AgSiNP nanoformulation. This assay uses two fluorescent dyes, STYO9 (green-emitting dye) and propidium iodide (red-emitting dye). The STYO9 labeling will confirm the presence of intact bacterial cell membrane (viable cells). The propidium iodide (a nuclear staining agent) labeling will indicate successful penetration of the dye through the compromised cell membrane (non-viable cells). Fluorescence confocal images (FIG. 1.10, FIG. 1.11 and FIG. 1.12) show the live/dead cell viability test results against *E. coli, B. subtilis* and *S. aureus* for AgSiNP200 nanoformulation and the SiNP control. Within 2 hours of incubation, it was observed that the non-viable cell population was increased for AgSiNP treated bacterial samples in comparison to SiNP control. This suggests that AgSiNP formulations possess strong antibacterial efficacy. Outstanding aqueous stability of the AgSiNP formulation at pH 7.0 is attributed to hydrophilic silica coating.

Conclusions

Stable Ag loaded silica nanoparticle formulations have been prepared using sol-gel method. The UV-Vis spectroscopic data confirmed loading of Ag in both ionic and AgNP forms. The SEM images confirmed the formation of monodispersed nanoparticles. The HRTEM study confirmed the formation of nearly spherical polycrystalline AgNPs. The DLS results showed relatively broad particle size distribution which is attributed to particle aggregation. The SEM images indeed show the presence of aggregated particles along with non-aggregated particles. This SEM results were in agreement with the DLS results. Strong antibacterial efficacy of the AgSiNP formulations was observed against three different microorganisms, E. coli, B. subtilis and S. aureus. The antibacterial efficacy of the AgSiNP formulations was comparable to the Ag nitrate control. This suggests that silica matrix did not compromise the antibacterial property of the Ag. As expected, no antibacterial properties was observed for SiNPs. The AgSiNP formulations were stable for months with no reduction in antibacterial efficacy. The present formulations should be useful for "touch-safe" antimicrobial spray coating applications.

REFERENCES

Each of which is Incorporated Herein by Reference

1. D. Lee, R. E. Cohen, M. F. Rubner, Antibacterial properties of Ag nanoparticle loaded multilayers and formation of magnetically directed antibacterial microparticles Langmuir 21, 9651-9659 (2005).
2. J. Costanza, A. M. El Badawy, T. M. Tolaymat, Comment on "120 Years of Nanosilver History: Implications for Policy Makers" Environmental Science & Technology 45, 7591-7592 (2011).
3. J. L. Clement, P. S. Jarrett, Antibacterial silver Metal-based drugs 1, 467-482 (1994).
4. R. Kumar, S. Howdle, H. Munstedt, Polyamide/silver antimicrobials: Effect of filler types on the silver ion release Journal of Biomedical Materials Research Part B-Applied Biomaterials 75B, 311-319 (2005).
5. K. H. Cho, J. E. Park, T. Osaka, S. G. Park, The study of antimicrobial activity and preservative effects of nanosilver ingredient Electrochimica Acta 51, 956-960 (2005).
6. B. Galeano, E. Korff, W. L. Nicholson, Inactivation of vegetative cells, but not spores, of *Bacillus anthracis*, B-cereus, and B-subtilis on stainless steel surfaces coated with an antimicrobial silver- and zinc-containing zeolite formulation Applied and Environmental Microbiology 69, 4329-4331 (2003).
7. Q. L. Feng, J. Wu, G. Q. Chen, F. Z. Cui, T. N. Kim, J. O. Kim, A mechanistic study of the antibacterial effect of silver ions on *Escherichia coli* and *Staphylococcus aureus* Journal of Biomedical Materials Research 52, 662-668 (2000).
8. S. Y. Liau, D. C. Read, W. J. Pugh, J. R. Furr, A. D. Russell, Interaction of silver nitrate with readily identifiable groups: relationship to the antibacterial action of silver ions Letters in Applied Microbiology 25, 279-283 (1997).
9. R. Kumar, H. Munstedt, Silver ion release from antimicrobial polyamide/silver composites Biomaterials 26, 2081-2088 (2005).
10. X. Xu, Q. Yang, Y. Wang, H. Yu, X. Chen, X. Jing, Biodegradable electrospun poly(L-lactide) fibers containing antibacterial silver nanoparticles European Polymer Journal 42, 2081-2087 (2006).
11. M. L. Di Lorenzo, M. Cocca, M. Malinconico, Crystal polymorphism of poly(L-lactic acid) and its influence on thermal properties Thermochimica Acta 522, 110-117 (2011).
12. R. J. Qu, M. G. Wang, C. M. Sun, Y. Zhang, C. A. Ji, H. Chen, Y. F. Meng, P. Yin, Chemical modification of silica-gel with hydroxyl- or amino-terminated polyamine for adsorption of Au(III) Applied Surface Science 255, 3361-3370 (2008).
13. C. Durucan, B. Akkopru, Effect of Calcination on Microstructure and Antibacterial Activity of Silver-Containing Silica Coatings Journal of Biomedical Materials Research Part B-Applied Biomaterials 93B, 448-458 (2010).
14. A. Hilonga, J. K. Kim, P. B. Sarawade, D. V. Quang, G. Shao, G. Elineema, H. T. Kim, Silver-doped silica powder with antibacterial properties Powder Technology 215-16, 219-222 (2012).
15. M. Jasiorski, A. Leszkiewicz, S. Brzezinski, G. Bugla-Ploskonska, G. Malinowska, B. Borak, I. Karbownik, A. Baszczuk, W. Strek, W. Doroszkiewicz, Textile with silver silica spheres: its antimicrobial activity against *Escherichia coli* and *Staphylococcus aureus* Journal of Sol-Gel Science and Technology 51, 330-334 (2009).
16. H. J. Jeon, S. C. Yi, S. G. Oh, Preparation and antibacterial effects of Ag—SiO2 thin films by sol-gel method Biomaterials 24, 4921-4928 (2003).
17. M. Kawashita, S. Tsuneyama, F. Miyaji, T. Kokubo, H. Kozuka, K. Yamamoto, Antibacterial silver-containing silica glass prepared by sol-gel method Biomaterials 21, 393-398 (2000).
18. Y. H. Kim, C. W. Kim, H. G. Cha, B. K. Jo, G. W. Ahn, E. S. Hong, Y. S. Kang, Preparation of antibacterial silver-containing silica nanocomposite Surface Review and Letters 15, 117-122 (2008).
19. S. Tarimala, N. Kothari, N. Abidi, E. Hequet, J. Fralick, L. L. Dai, New approach to antibacterial treatment of cotton fabric with silver nanoparticle-doped silica using sol-gel process Journal of Applied Polymer Science 101, 2938-2943 (2006).
20. C. S. Wu, H. T. Liao, Antibacterial Activity and Antistatic Composites of Polyester/Ag—SiO2 Prepared by a Sol-Gel Method Journal of Applied Polymer Science 121, 2193-2201 (2011).
21. S. Egger, R. P. Lehmann, M. J. Height, M. J. Loessner, M. Schuppler, Antimicrobial Properties of a Novel Silver-Silica Nanocomposite Material Applied and Environmental Microbiology 75, 2973-2976 (2009).
22. K. Xu, J. X. Wang, X. L. Kang, J. F. Chen, Fabrication of antibacterial monodispersed Ag—SiO(2) core-shell nanoparticles with high concentration Materials Letters 63, 31-33 (2009).
23. K. Chamakura, R. Perez-Ballestero, Z. P. Luo, S. Bashir, J. B. Liu, Comparison of bactericidal activities of silver nanoparticles with common chemical disinfectants Colloids and Surfaces B-Biointerfaces 84, 88-96 (2011).
24. X. Chen, H. J. Schluesener, Nanosilver: A nanoproduct in medical application Toxicology Letters 176, 1-12 (2008).
25. J. Q. Hu, Q. Chen, Z. X. Xie, G. B. Han, R. H. Wang, B. Ren, Y. Zhang, Z. L. Yang, Z. Q. Tian, A simple and effective route for the synthesis of crystalline silver nanorods and nanowires Advanced Functional Materials 14, 183-189 (2004).
26. C. Krishnaraj, R. Ramachandran, K. Mohan, P. T. Kalaichelvan, Optimization for rapid synthesis of silver nanoparticles and its effect on phytopathogenic fungi Spectrochimica Acta Part a-Molecular and Biomolecular Spectroscopy 93, 95-99 (2012).
27. P. Manivel, A. Balamurugan, N. Ponpandian, D. Mangalaraj, C. Viswanathan, Novel synthesis of silver nanoparticles using 2,3,5,6-tetrakis-(morpholinomethyl)hydroquinone as reducing agent Spectrochimica acta. Part A, Molecular and biomolecular spectroscopy 95, 305-309 (2012).
28. D. Poondi, R. Subramanian, M. Otooni, J. Singh, Synthesis of silver nanoparticles by a laser-liquid-solid interaction technique Journal of Materials Synthesis and Processing 6, 89-104 (1998).
29. S. D. Solomon, M. Bahadory, A. V. Jeyarajasingam, S. A. Rutkowsky, C. Boritz, L. Mulfinger, Synthesis and study of silver nanoparticles Journal of Chemical Education 84, 322-325 (2007).
30.1. Tanahashi, M. Yoshida, Y. Manabe, T. Tohda, Effects of Heat treatment on Ag particle growth and optical-properties in Ag/SiO2 glass composite thin films Journal of Materials Research 10, 362-365 (1995).
31. M. Annadhasan, V. R. Sankarbabu, R. Naresh, K. Umamaheswari, N. Rajendiran, A sunlight-induced rapid synthesis of silver nanoparticles using sodium salt of N-cholyl amino acids and its antimicrobial applications Colloids and surfaces. B, Biointerfaces 96, 14-21 (2012).
32. R. Ciriminna, M. Sciortino, G. Alonzo, A. de Schrijver, M. Pagliaro, From Molecules to Systems: Sol-Gel Microencapsulation in Silica-Based Materials Chemical Reviews 111, 765-789 (2011).
33. N. Y. Hebalkar, S. Acharya, T. N. Rao, Preparation of bi-functional silica particles for antibacterial and self cleaning surfaces Journal of Colloid and Interface Science 364, 24-30 (2011).
34. K. S. Rao, K. El-Hami, T. Kodaki, K. Matsushige, K. Makino, A novel method for synthesis of silica nanoparticles Journal of Colloid and Interface Science 289, 125-131 (2005).
35. S. C. Tang, Y. F. Tang, F. Gao, Z. G. Liu, X. K. Meng, Ultrasonic electrodeposition of silver nanoparticles on dielectric silica spheres Nanotechnology 18 (2007).
36. S. C. Warren, M. R. Perkins, A. M. Adams, M. Kamperman, A. A. Burns, H. Arora, E. Herz, T. Suteewong, H. Sai, Z. H. Li, J. Werner, J. H. Song, U. Werner-Zwanziger, J. W. Zwanziger, M. Gratzel, F. J. DiSalvo, U. Wiesner, A silica sol-gel design strategy for nanostructured metallic materials Nature Materials 11, 460-467 (2012).
37. S. Pal, Y. K. Tak, J. M. Song, Does the antibacterial activity of silver nanoparticles depend on the shape of the nanoparticle? A study of the gram-negative bacterium *Escherichia coli* Applied and Environmental Microbiology 73, 1712-1720 (2007).
38. W. K. Jung, H. C. Koo, K. W. Kim, S. Shin, S. H. Kim, Y. H. Park, Antibacterial activity and mechanism of action of the silver ion in *Staphylococcus aureus* and *Escherichia coli* Applied and Environmental Microbiology 74, 2171-2178 (2008).
39. B. J. Frisken, Revisiting the method of cumulants for the analysis of dynamic light-scattering data Applied Optics 40, 4087-4091 (2001).
40. U. Schillinger, F. K. Lucke, Antibacterial Activity of *Lactobacillus*-Sake Isolated From Meat Applied and Environmental Microbiology 55, 1901-1906 (1989).
41. S. K. Rastogi, V. J. Rutledge, C. Gibson, D. A. Newcombe, J. R. Branen, A. L. Branen, Ag colloids and Ag clusters over EDAPTMS-coated silica nanoparticles: synthesis, characterization, and antibacterial activity against *Escherichia coli* Nanomedicine-Nanotechnology Biology and Medicine 7, 305-314 (2011).
42. T. J. Collins, ImageJ for microscopy Biotechniques 43, 25-30 (2007).
43. Z. Li, A. Gu, Q. Zhou, Growth of spindle-shaped silver nanoparticles in SDS solutions Crystal Research and Technology 44, 841-844 (2009).
44. R. R. Naik, S. J. Stringer, G. Agarwal, S. E. Jones, M. O, Stone, Biomimetic synthesis and patterning of silver nanoparticles Nature Materials 1, 169-172 (2002).
45. J. J. Mock, M. Barbic, D. R. Smith, D. A. Schultz, S. Schultz, Shape effects in plasmon resonance of individual colloidal silver nanoparticles Journal of Chemical Physics 116, 6755-6759 (2002).
46. Y. H. Kim, D. K. Lee, H. G. Cha, C. W. Kim, Y. S. Kang, Synthesis and characterization of antibacterial Ag—SiO2 nanocomposite Journal of Physical Chemistry C 111, 3629-3635 (2007).
47. R. Gupta, A. Kumar, Bioactive materials for biomedical applications using sol-gel technology Biomedical Materials 3 (2008).
48. K. Nischala, T. N. Rao, N. Hebalkar, Silica-silver core-shell particles for antibacterial textile application Colloids and Surfaces B-Biointerfaces 82, 203-208 (2011).

Example 2

Brief Introduction

Antimicrobial properties of copper (Cu) and silver (Ag) ions have been widely studied. Hundreds of nanotech based consumer products are now available in the market which uses antimicrobial Ag nanoparticles. Cu and Cu alloy based touch surfaces are shown to be effective in controlling bacterial infection. In this example, we will present our research on synthesis and characterization of sol-gel silica nanoparticle/nanogel materials loaded with antimicrobial Cu and Ag. Structure/morphology and antimicrobial properties of the silica nanoparticle/nanogel delivery system with and without containing the active agent (Cu or Ag) will be discussed. We have tested antimicrobial properties of these materials against both gram-negative (*E. Coli*) and gram-positive (*B. Subtilis*) bacteria. Our results on Cu nanomaterials showed improved antibacterial efficacy of Cu loaded silica nanomaterial over its Cu source while the concentration of metallic Cu remained the same. Several materials characterization techniques were used to understand structure-property relationship using Cu loaded silica nanoparticle/nanogel nanomaterial.

Introduction:

Metallic nanoparticles have been used recently for a wide range of biomedical applications[1,2]. Silver and copper have been known for ages for its antimicrobial properties. Copper and silver are being used as antifouling, antifungal agents for many industrial applications. Their antibacterial property finds wide usage in many health-care facilities to create microorganism free environment. Various techniques are being used for synthesis of metallic nanoparticles. They include inert gas condensation technique, electrolysis method, deposition of metallic salts on the matrix, reduction of metallic salt[3-7]. This paper is focused on the synthesis, characterization and antibacterial properties of silica-silver nanogel and silica-copper nanoparticles by acid and base hydrolysis respectively. Silver embedded silica nanogel is synthesized using simple water based sol-gel technology. In this method the simultaneous hydrolysis and condensation of silica facilitates the reduction of silver ions to form silver nanoparticles entrapped in silica gel matrix[8]. Copper nanoparticles are synthesized based on a novel core-shell design, where the silica nanoparticle serves as the 'core' and copper grows as the 'shell' around the core[9].

EXPERIMENTAL

All reagents were purchased from commercial vendors and used without any further purification. Bacterial strains were provided by Ishrath Sharma, Microbiology department, University of Central Florida.

Nanomaterial Synthesis

The core-shell copper loaded silica nanoparticles (C—S CuSiNP) were synthesized in a two-step fashion as discussed in our previous work[9]. The first step involved the synthesis of 'seed' silica nanoparticles based on a published protocol[10]. Tetraethylorthosilicate (TEOS, a silane precursor; Fisher Scientific) was added to a solution of 95% ethanol (Fisher Scientific), ammonium hydroxide (Fisher Scientific) and water (nanopure deionized) under stirring conditions. The contents were left on a 400 rpm magnetic stirrer for 1 hour. This was followed by sonication for 10 minutes. The silica nanoparticles (SiNP) were purified by washing (centrifuging) the particles with 95% ethanol at 10,000 rpm for 10 minutes to remove ammonium hydroxide. The final wash (10,000 rpm, 10 minutes) was done with water. The second step involved the growth of copper shell around the silica nanoparticle core. The silica 'seed' particles were dispersed in acidic pH water followed by addition of copper sulfate pentahydrate (CQ concepts, Ringwood, Ill.) and TEOS under magnetic stirring conditions. The growth of the copper 'shell' around the silica nanoparticle 'core' was allowed to grow for 24 hours. The particles were then isolated by washing (centrifugation) with water twice at 10,000 rpm for 10 minutes to remove excess copper.

The synthesis of silver loaded silica nanogel (AgSiNG) was carried on using sol-gel method in water and acidic condition in one step[11]. This procedure was similar to the second step of C—S CuSiNP synthesis as described in the above section. Silver nitrate salt (Acros organics) was used as the source of Ag and 1% Nitric acid (Macron) solution was used for the acid catalyzed hydrolysis of TEOS. Silica nanogel (SiNG) was prepared similarly (without silver nitrate) which was used as control. No further purifications were made to AgSiNG and SiNG materials except that the pH was adjusted to 7.0 using dilute sodium hydroxide solution. A pale yellow coloration was observed for the AgSiNG material.

Nanomaterial Characterization

Zeiss ULTRA-55 FEG Scanning electron microscopy (SEM) was done to estimate the particle size and morphology of C—S CuSiNP. Spin coating technique was used to prepare the SEM sample on a silicon wafer. The amount of copper in C—S CuSiNP was quantified by Atomic Absorption Spectroscopy (AAS, Perkin Elmer AAnalyst 400 AA spectrometer). The metallic silver content in AgSiNG was quantified from the amount of silver nitrate added in the formulation. The AgSiNG formulation was completely transparent and the material could not be centrifuged down from the solution even at 10,000 rpm. Therefore the AgSiNG formulation was used for antimicrobial studies without any further purification. High-resolution transmission electron microscopy (HRTEM, Technai) technique was used to analyze AgSiNG material for the formation of silver nanoparticles. Sample was prepared by placing a drop of AgSiNG on a carbon coated copper grid.

Antibacterial Assays

Antibacterial properties of C—S CuSiNP and AgSiNG materials were evaluated against a gram positive *Bacillus subtilis* (*B. subtilis*, ATCC 9372) and a gram negative *Escherichia coli* (*E. coli*, ATCC 35218) organism. For all antibacterial assays, bacterial concentration of $10^5$ cells/mL was considered. Copper sulfate with same metallic copper concentration was used as positive controls and silica nanoparticle (without Cu loading) was used as negative control. In case of AgSiNG, silver nitrate with similar metallic silver concentration was used as positive control and silica gel (without silver) was used as negative control.

(i) Bacterial Growth Inhibition in LB Broth Using Turbidity

Two sets of different concentrations of C—S CuSiNP were made in LB broth (0.49, 1.2, 2.4, 4.9, 7.2 and 9.8 ppm copper concentration) to a final volume of 10 mL. 250 µL ($10^5$ cells/mL) of *E. coli* and *B. subtilis* were added to set 1 and 2 respectively. Silica nanoparticle was used as negative control and copper sulfate with equivalent amount of copper was used as positive control. All the tubes were incubated at 37° C. on a shaker at 150 rpm for 24 hours. Aliquots were taken after 24 hours to measure optical density at 600 nm. The same was repeated for AgSiNG.

(ii) Bac-Light Assay for Live/Dead Cell Staining

A known concentration of C—S CuSiNP and AgSiNP with appropriate controls was incubated with *E. coli* and *B. subtilis* in LB broth ($10^5$ cells/mL) to determine cell viability using the BacLight bacterial viability kit L7012[12]. The samples were incubated for 4 hours at 37° C. on 150 rpm shaker. The samples were then centrifuged at 10,000×g for 10 minutes. The supernatant was discarded and resuspended in 0.85% saline and centrifuged again. The final pellet was resuspended in 0.85% saline. 3 µL of the baclight dye mixture was added to all tubes and incubated at room temperature in dark for 15 minutes. 5 µL of the bacterial suspension was trapped between a slide and coverslip and viewed under a fluorescence microscope. The dead and live cells are counted using the red and green filters respectively.

Results and Discussion

Nanomaterial Characterization

The SEM images of the 'core' SiNP (an average particle size of ~380 nm) and the C—S CuSiNP (an average particle size of ~450 nm) are shown in FIG. 2.1a and FIG. 2.1b, respectively. The increase in particle size and spherical morphology for C—S CuSiNP confirms uniform growth of copper loaded shell on the silica nanoparticle core with a shell thickness of ~50 nm. Copper in C—S CuSiNP is chelated by the silica silanol (Si—OH) groups in the silica matrix forming a weak Cu—Si complex. However, the reduction mechanism of copper is not well understood as no specific reducing agent was added externally during the synthesis process. However, it is possible that ethanol (which is produced after the TEOS hydrolysis) and silica (with —OH and —O⁻ groups) might have played a role of mild reducing agents. Atomic Absorption Spectroscopy (AAS) quantified the amount of copper to be 0.098 ppm in comparison to copper standards. FIG. 2.2a shows the HRTEM micrograph of AgSiNG. The formation of silver nanoparticles ranging from 10-20 nm uniformly distributed in amorphous silica matrix (grey material in contrast) was confirmed by the HRTEM. The HRTEM-selected area electron diffraction pattern confirms crystallinity of the silver nanoparticles along with lattice planes of 2.36±0.05 Å for 111 and 2.04±0.04 for 200 specific for Ag. Additionally we also identified 220 and 311 reflections in electron diffraction pattern that are specific for Ag crystals (FIG. 2.2b). The formation of Ag nanoparticles can be accounted to addition of sodium hydroxide in the formulation that acted as a reducing agent[13] to reduce $Ag^+$ to $Ag^0$ leading addition of metallic Ag to produce Ag nanoparticles.

Antibacterial Assays

The growth inhibitory effects of C—S CuSiNP and AgSiNG against *E. coli* and *B. subtilis* were studied in liquid media (FIG. 2.3 and FIG. 2.4). Bacterial growth with different concentrations of C—S CuSiNP and AgSiNG (0.49 to 9.8 µg mL$^{-1}$) was monitored after 24 hours of incubation at 37° C. by measuring the optical density at 600 nm using Teysche800 spectrophotometer. Since the turbidity of silica based material can interfere with the optical density reading, the background measurement was subtracted to calculate the final reading.

C—S CuSiNP showed significant growth inhibition of two different strains of bacterium, gram-negative *E. coli* and gram-positive *B. subtilis*. Total inhibition was obtained at 9.8 ppm copper concentration for both the bacterium. C—S CuSiNP exhibited improved antibacterial efficacy in comparison to copper sulfate against *E. coli* as well as *B. subtilis*. This clearly shows that C—S CuSiNP has improved copper bioavailability when compared to copper sulfate with similar copper concentration. This could be attributed to the novel core-shell design, where majority of the copper is present in the shell. C—S CuSiNP is intermediate between "soluble" and "insoluble" copper compounds where the Cu ions are chelated in the silica matrix. This results in improved and sustained antibacterial activity in comparison to "soluble" copper sulfate.

In case of AgSiNG higher growth inhibition could be seen in *E. coli* (FIG. 2.5) than compared to *B. subtilis* (FIG. 2.6), this could be attributed to the difference in the cell wall structure of the bacteria. No statistically significant difference in the antibacterial efficacy was observed between the AgSiNG and the silver nitrate materials, suggesting that silica matrix served as a host matrix and did not compromise the antibacterial properties of silver. The growth inhibition can be seen at 2.4 ppm of silver in both AgSiNG and silver nitrate solutions. This corresponds to the value of MIC of silver[14]. Thus it can be seen that embedding silver in silica did not interrupt the antibacterial properties of silver ions.

Baclight live/dead cell staining was also done using ZEISS Axioskop2 confocal microscope to determine the cell viability of *E. coli* and *B. subtilis*. The images of live/dead cells with different concentrations of C—S CuSiNP were taken using a florescent microscope (FIG. 2.7). Similarly images were taken for the bacteria incubated with different concentrations of AgSiNG using fluorescent microscope (FIG. 2.8). The green filter (535 nm) was used to view live cells and red filter (642 nm) was used to view dead cells. The amount of red cells was significantly greater than the green cells, confirming the bactericidal effect of the metallic based silica nanogel nanoparticle material.

CONCLUSION

Using a simple sol-gel method, core-shell copper loaded silica nanoparticle (C—S CuSiNP, ~450 nm) and silver loaded silica nanogel materials embedding 10-20 nm size crystalline silver nanoparticles have been successfully synthesized. In comparison to copper sulfate control, C—S CuSiNP material showed improved antibacterial properties against both *E. coli* (a gram-negative) and *B. subtilis* (a gram-positive) bacteria. This has been attributed to improved Cu bioavailability of C—S CuSiNP material where the core-shell design could have been played an important role. Antibacterial efficacy of silver did not compromise in AgSiNG material, suggesting that silica matrix served simply as a host material. The present study demonstrates that the silica matrix can be efficiently used as an inert delivery vehicle for metal based antibacterial active agents such as copper and silver as both nanoparticle and nanogel matrix formats.

REFERENCES

Each of which is Incorporated Herein by Reference

1. G. Borkow, J. Gabbay, Copper as a biocidal tool Current Medicinal Chemistry 12, 2163-2175 (2005).
2. Y. Kobayashi, T. Sakuraba, Silica-coating of metallic copper nanoparticles in aqueous solution Colloids and Surfaces A: Physicochemical and Engineering Aspects 317, 756-759 (2008).
3. P. Appendini, J. H. Hotchkiss, Review of antimicrobial food packaging Innovative Food Science & Emerging Technologies 3, 113-126 (2002).
4. M. H. Freeman, C. R. McIntyre, A comprehensive review of copper-based wood preservatives: with a focus on new micronized or dispersed copper systems Forest Products Journal 58, 6-27 (2008).
5. T. P. Schultz, D. D. Nicholas, A. F. Preston, A brief review of the past, present and future of wood preservation Pest Manage. Sci. 63, 784-788 (2007).
6. A. Singh, V. Krishna, A. Angerhofer, B. Do, G. MacDonald, B. Moudgil, Copper Coated Silica Nanoparticles for Odor Removal Langmuir 26, 15837-15844 (2010).
7. N. Voulvoulis, M. D. Scrimshaw, J. N. Lester, Alternative antifouling biocides Applied Organometallic Chemistry 13, 135-143 (1999).
8. D. V. Quang, P. B. Sarawade, A. Hilonga, J.-K. Kim, Y. G. Chai, S. H. Kim, J.-Y. Ryu, H. T. Kim, Preparation of silver nanoparticle containing silica micro beads and investigation of their antibacterial activity Applied Surface Science 257, 6963-6970 (2011).
9. P. Maniprasad, S. Santra, Novel copper (Cu) loaded core-shell silica nanoparticles with improved Cu bioavailability: synthesis, characterization and study of antibacterial properties Journal of Biomedical Nanotechnology (accepted on Dec. 24, 2011) (2012).
10. L. M. Rossi, L. F. Shi, F. H. Quina, Z. Rosenzweig, Stober synthesis of monodispersed luminescent silica nanoparticles for bioanalytical assays Langmuir 21, 4277-4280 (2005).
11. M. Kawashita, S. Tsuneyama, F. Miyaji, T. Kokubo, H. Kozuka, K. Yamamoto, Antibacterial silver-containing silica glass prepared by sol, Äìgel method Biomaterials 21, 393-398 (2000).
12. S. K. Rastogi, V. J. Rutledge, C. Gibson, D. A. Newcombe, J. R. Branen, A. L. Branen, Ag colloids and Ag clusters over EDAPTMS-coated silica nanoparticles: synthesis, characterization, and antibacterial activity against *Escherichia coli* Nanomedicine: Nanotechnology, Biology and Medicine 7, 305-314 (2011).
13. D. T. Sawyer, J. L. Roberts, Hydroxide ion: an effective one-electron reducing agent? Accounts of Chemical Research 21, 469-476 (1988).
14. S. Egger, Lehmann, R. P., Height, M. J., Loessner, M. J., & Schuppler, M., Antimicrobial properties of a novel silver-silica nanocomposite material. Applied and Environmental Microbiology 75, 2973-2976 (2009).

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to measurement techniques and the numerical value. In addition, the phrase "about 'x' to 'y'" includes "about 'x' to about 'y'".

Many variations and modifications may be made to the above-described embodiments. All such modifications and variations are intended to be included herein within the scope of this disclosure and protected by the following claims.

Therefore, at least the following is claimed:

1. A composition, comprising a silver/silica nanocomposite having a silica matrix that includes silver from one or more of silver nanoparticles and silver ions, along with interconnected silica particles, wherein a UV-visible optical spectrum of the silver/silica nanocomposite in a neutral aqueous carrier has at least a bimodal optical absorption, wherein the bimodal optical absorption comprises:
    a first absorption peak at about 295 to about 296 nanometers, and
    a second absorption peak at about 419 to about 421 nanometers, when the silver/silica nanocomposite has a silver content from 10.59 to 24.19 weight percent.

2. The composition of claim 1, wherein the silver/silica nanocomposite is transparent to visible light.

3. The composition of claim 1, wherein the silver nanoparticles have a diameter of about 5 to 20 nm.

4. The composition of claim 1, wherein the silica matrix includes silver ions ionically bonded to silica nanoparticles.

5. The composition of claim 1, wherein the silica matrix is disposed around the entire silver nanoparticle.

6. A composition comprising;
    a carrier; and
    a silver/silica nanocomposite contained within the carrier, wherein a UV-visible optical spectrum of the silver/silica nanocomposite in a neutral aqueous carrier comprises at least a bimodal optical absorption, wherein the bimodal optical absorption comprises:
    a first absorption peak at about 295 to about 296 nanometers; and
    a second absorption peak at about 419 to about 421 nanometers, when the silver/silica nanocomposite has a silver content from 10.59 to 24.19 weight percent.

7. A composition comprising:
    a neutral aqueous carrier; and
    a silver/silica nanocomposite contained within the neutral aqueous carrier, where a UV-visible optical spectrum of the silver/silica nanocomposite in the neutral aqueous carrier comprises at least a bimodal optical absorption, wherein the bimodal optical absorption comprises:
    a first absorption peak at about 295 to about 296 nanometers; and
    a second absorption peak at about 419 to about 421 nanometers, when the silver/silica nanocomposite has a silver content from 10.59 to 24.19 weight percent.

8. The composition of claim 1 wherein the first absorption peak is taller than the second absorption peak.

9. The composition of claim 1 wherein the composition consists essentially of the silver/silica nanocomposite.

10. The composition of claim 1 wherein the silica matrix comprises a silica gel matrix.

11. The composition of claim 7 wherein the silver is present in the composition about 10 nanogram (ng)/mL to 100 milligram (mg)/mL of the silver/silica nanocomposite with respect to the neutral aqueous carrier.

* * * * *